(12) United States Patent
Schepis et al.

(10) Patent No.: US 10,478,612 B2
(45) Date of Patent: Nov. 19, 2019

(54) METHOD AND SYSTEM FOR MONITORING AND TREATING A MEDICAL CONDITION VIA POSTERIOR TIBIAL NERVE STIMULATION

(71) Applicant: Avent, Inc., Alpharetta, GA (US)

(72) Inventors: Eric A. Schepis, Alpharetta, GA (US); Nicole Y. Dumas, Woodstock, GA (US); Martha L. Tate, Sandy Springs, GA (US)

(73) Assignee: Avent, Inc., Alpharetta, GA (US)

( * ) Notice: Subject to any disclaimer, the term of this patent is extended or adjusted under 35 U.S.C. 154(b) by 158 days.

(21) Appl. No.: 15/523,128

(22) PCT Filed: Oct. 28, 2015

(86) PCT No.: PCT/US2015/057707
§ 371 (c)(1),
(2) Date: Apr. 28, 2017

(87) PCT Pub. No.: WO2016/069687
PCT Pub. Date: May 6, 2016

(65) Prior Publication Data
US 2017/0326351 A1    Nov. 16, 2017

Related U.S. Application Data

(60) Provisional application No. 62/073,412, filed on Oct. 31, 2014.

(51) Int. Cl.
*A61N 1/00* (2006.01)
*A61N 1/04* (2006.01)
*A61N 1/36* (2006.01)

(52) U.S. Cl.
CPC ......... *A61N 1/0456* (2013.01); *A61N 1/0484* (2013.01); *A61N 1/36014* (2013.01)

(58) Field of Classification Search
CPC . A61N 1/0456; A61N 1/0484; A61N 1/36014
See application file for complete search history.

(56) References Cited

U.S. PATENT DOCUMENTS

| 8,958,886 B2 | 2/2015 | Schepis et al. |
| 2005/0070971 A1 | 3/2005 | Fowler et al. |

(Continued)

FOREIGN PATENT DOCUMENTS

| GB | 2473478 A | 3/2011 |
| WO | WO 2011/158018 A1 | 12/2011 |

(Continued)

OTHER PUBLICATIONS

Bellette, et al., Posterior Tibial Nerve Stimulation in the Management of Overactive Bladder. A Prospective and Controlled Study, Urology Service of the Medical Faculty of State of University of Campinas-Unicamp, Brazil, vol. 33(1), 2009, 11 pages.

(Continued)

*Primary Examiner* — Lindsey G Wehrheim
(74) *Attorney, Agent, or Firm* — Dority & Manning, P.A.

(57) ABSTRACT

Various systems and methods for non-invasively monitoring and treating a medical condition of interest via transcutaneous stimulation of a target nerve are described. For instance, a subject can be monitored for improvement of a medical condition, where such improvement corresponds with a decrease in the threshold level at which a sensory or motor response is elicited in a subject upon stimulation as compared to a baseline level. Further, transcutaneous stimulation of the nerve can also treat the condition. Both monitoring and treatment can be carried out in a non-invasive manner substantially free of a painful response via electrical nerve stimulation of a target nerve, where the stimulation is delivered from an electrode placed on a non-glabrous skin surface. The electrode placement sufficiently immobilizes (Continued)

the target nerve such that the stimulation is effective and can be delivered in a controlled manner.

20 Claims, 12 Drawing Sheets

(56) References Cited

U.S. PATENT DOCUMENTS

| | | | |
|---|---|---|---|
| 2008/0091114 A1* | 4/2008 | Min | A61B 5/0537 600/508 |
| 2009/0326607 A1 | 12/2009 | Castel et al. | |
| 2010/0137961 A1 | 6/2010 | Moffitt et al. | |
| 2012/0101326 A1 | 4/2012 | Simon et al. | |
| 2013/0006322 A1* | 1/2013 | Tai | A61N 1/36014 607/39 |
| 2013/0085317 A1 | 4/2013 | Feinstein | |

FOREIGN PATENT DOCUMENTS

| | | |
|---|---|---|
| WO | WO 2012/040243 A1 | 3/2012 |
| WO | WO 2013/102056 A1 | 7/2013 |
| WO | WO 2014/151431 A2 | 9/2014 |

OTHER PUBLICATIONS

Biemans, et al., Efficacy and Effectiveness of Percutaneous Tibial Nerve Stimulation in the Treatment of Pelvic Organ Disorders: A Systematic Review, Neuromodulation: Technolgoy at the Neural Interface. 2012, 10 pages.

Krivoborodov, et al., Afferent stimulation of the tibial nerve in Patients with Overactive Bladder, Department of Urology, Medical University, Moscow, 2002: 16 pages.

Mazo et al., Sacred time and tibial neuromodulation in treating patients with overactive bladder, Department of Urology, Medical University, Moscow, 2002, 20 pages.

Nakamura, et al., Transcutaneous Electrical Stimulation for the Control of Frequency and Urge Incontinence, Department of Urology, Osaka Koseinenkin Hospital, Apr. 26, 1983, 11 pages.

Paper, Translation of Transcutaneous Electrical Stimulation document, Apr. 26, 1983, 7 pages.

International Search Report for PCT/US2015/057707, dated Apr. 25, 2016, 4 pages.

* cited by examiner

METHOD AND SYSTEM FOR MONITORING AND TREATING A MEDICAL CONDITION VIA POSTERIOR TIBIAL NERVE STIMULATION

RELATED APPLICATIONS

The present application is the national stage entry of International Patent Application No. PCT/US2015/057707 having a filing date of Oct. 28, 2015, which claims priority to U.S. Provisional Patent Application Ser. No. 62/073,412, filed on Oct. 31, 2014, both of which are incorporated herein in their entirety by reference thereto.

BACKGROUND

Medical conditions such as bladder disorders, bowel disorders, and sexual disorders affect the quality of life of millions of people in the United States and across the world. Turning to bladder disorders specifically, overactive bladder is a condition in which involuntary bladder contractions occur during bladder filling despite a person's attempt to suppress them. It causes symptoms such as urinary frequency and nocturia. Urge incontinence, which is the unintentional loss of urine caused by the bladder muscle contracting, and is usually associated with a sense of urgency, may also occur, as can stress incontinence. Stress incontinence happens when physical movement or activity (coughing, sneezing, running, etc.) puts pressure on the bladder and is distinguished from urge incontinence. The prevalence of urinary disorders such as overactive bladder, urge incontinence, and stress incontinence and their impact on quality of life is substantial, necessitating better treatment options. In addition, bowel disorders such as bowel incontinence or irritable bowel syndrome also affect the quality of life of many people, as can sexual disorders such as erectile dysfunction in some men, detrusor over-activity resulting in coital incontinence in some women, or persistent sexual arousal syndrome. The aforementioned urinary, bowel, and sexual disorders, which are associated with the pelvic region, can manifest themselves individually or in combination with each other. For instance, patients suffering from urge and/or stress incontinence may also suffer from bowel incontinence, while patients suffering from overactive bladder may also suffer from persistent sexual arousal syndrome.

Various treatments, for example, are available to mitigate bladder disorders such as overactive bladder, urge continence, or stress incontinence. Milder treatment options include lifestyle changes, bladder training, and pelvic floor exercises (i.e. kegel exercises). Such treatment options can also be used to mitigate bowel disorders or sexual disorders. Although these methods may help the person suffering from such disorders, they are time consuming and are often unsuccessful. Other treatment options include medication, surgery, and neuromodulation. Medication may not be desirable for some patients because of contraindications or lack of compliance. Surgery is reserved for persons that are severely affected by the aforementioned disorders because of possible complications such as blood clots, bowel obstruction, infection, and pneumonia. Neuromodulation treatments to mitigate bladder disorders, bowel disorders, and sexual disorders are showing promise and have become more popular.

Neuromodulation technologies use electrical stimulation to modulate nerves that are positioned deep beneath the skin's surface. The systems deliver electrical stimulation to the sacral, tibial, or pudendal nerves to modulate micturition (i.e. spinal) reflexes that are responsible for controlling the pelvic region where bladder disorders, bowel disorders, and sexual disorders manifest. Stimulation is delivered to these nerves either directly (i.e. invasively) or indirectly, and acts on different parts of the reflex pathway, yielding different outcomes. The use of such technology can be effective in the treatment of persons with bladder disorders as well as persons with bowel disorders, or sexual disorders, including persons who have failed pharmacological therapies. Invasive procedures are expensive and can lead to surgical complications, while non-invasive procedures can be painful or cause discomfort.

As such, there remains a need for a safe, effective, and non-invasive method to monitor and treat the symptoms of bladder disorders, bowel disorders, or sexual disorders that can be administered by an individual with or without the assistance of a doctor, nurse, or other medical professional in an efficient manner and without causing the individual pain.

SUMMARY

Disclosed is a method for non-invasively monitoring a medical condition in a subject. The method includes positioning a first electrode adjacent to a surface of non-glabrous skin, wherein the first electrode is a cathode; and positioning a second electrode adjacent to a surface of non-glabrous or glabrous skin, wherein the second electrode is an anode spaced apart a predetermined distance from the first electrode. The method further includes transcutaneously delivering a first electrical nerve stimulation to a target nerve via the first electrode and the second electrode; and determining a baseline current or a baseline voltage for the subject, wherein the baseline current is the current at which a sensory response or a motor response is elicited in the subject as a result of the first electrical nerve stimulation, and wherein the baseline voltage is the voltage at which a sensory response or a motor response is elicited in the subject. In addition, the method includes transcutaneously delivering a second electrical nerve stimulation to the target nerve via the first electrode and the second electrode; and determining a threshold current or a threshold voltage for the subject, wherein the threshold current is the current at which a sensory response or a motor response is elicited in the subject as a result of the second electrical nerve stimulation, and wherein the threshold voltage is the voltage at which a sensory response or a motor response is elicited in the subject. The method then includes comparing the threshold current to the baseline current or the threshold voltage to the baseline voltage, wherein the medical condition is improved if the threshold current is lower than the baseline current or the threshold voltage is lower than the baseline voltage.

In one embodiment of the method, the non-glabrous skin can be located at an ankle of the subject proximate a medial malleolus and at least partly overlies a flexor retinaculum. Further, the non-glabrous skin can at least partly overlie a cephalic border of the flexor retinaculum.

In one aspect, the method further comprises positioning a compressive device over the first electrode to immobilize the target nerve.

In another aspect, the target nerve can emanate from the sacral plexus. For instance, the target nerve can be the posterior tibial nerve.

In one more aspect of the method, the first electrode can have a skin-contacting surface having an area of from about 0.75 mm$^2$ to about 2000 mm$^2$.

In an additional aspect of the method, the baseline current can be about 25 milliamps or less for a sensory response or can be about 50 milliamps or less for a motor response.

In another embodiment of the method, the baseline voltage can be about 150 volts or less for a sensory response or can be about 300 volts or less for a motor response.

In one particular embodiment of the method, the first electrical nerve stimulation and the second electrical nerve stimulation can be delivered at a current of about 0.1 milliamps, where the current is incrementally increased until the baseline current and the threshold current are determined.

In one more aspect of the method, the first electrical nerve stimulation and the second electrical nerve stimulation can be delivered at a voltage of about 0.1 volts, wherein the voltage is incrementally increased until the baseline voltage and the threshold voltage are determined.

In yet another aspect of the method, the first electrical nerve stimulation and the second electrical nerve stimulation can be delivered at a frequency ranging from about 0.1 Hertz to about 50 Hertz.

In one aspect of the method, the medical condition can be a urinary disorder, a bowel disorder, or a sexual disorder. For instance, the urinary disorder can be overactive bladder, urge incontinence, stress incontinence, or a combination thereof; the bowel disorder can be bowel incontinence or irritable bowel syndrome; and the sexual disorder can be erectile dysfunction, detrusor over-activity, or persistent sexual arousal syndrome.

In another aspect, disclosed is a system for non-invasively monitoring a medical condition in a subject via stimulation of a target nerve. The system includes a first electrode, a second electrode, and an electronic control system. The first electrode is configured for placement on a surface of non-glabrous skin, wherein the first electrode is a cathode. Meanwhile, the second electrode is configured for placement on a surface of non-glabrous or glabrous skin, wherein the second electrode is an anode. The electronic control system is coupled to the first electrode and the second electrode. The electronic control system is configured to: transcutaneously deliver a first electrical nerve stimulation to the target nerve via the first electrode and the second electrode to determine a baseline current or a baseline voltage for the subject, wherein the baseline current is the current at which a sensory response or a motor response is elicited in the subject as a result of the first electrical nerve stimulation, and wherein the baseline voltage is the voltage at which a sensory response or a motor response is elicited in the subject; and transcutaneously deliver a second electrical nerve stimulation to the target nerve via the first electrode and the second electrode to determine a threshold current or a threshold voltage for the subject, wherein the threshold current is the current at which a sensory response or a motor response is elicited in the subject as a result of the second electrical nerve stimulation, and wherein the threshold voltage is the voltage at which a sensory response or a motor response is elicited in the subject, wherein the medical condition is improved if the threshold current is lower than the baseline current or the threshold voltage is lower than the baseline voltage.

In one particular aspect of the system, the non-glabrous skin can be located at an ankle of the subject proximate a medial malleolus and can at least partly overlie a flexor retinaculum. Further, the non-glabrous skin can at least partly overlie a cephalic border of the flexor retinaculum.

In another aspect, the system can also include a compressive device, where the compressive device is configured for placement over the first electrode to immobilize the target nerve.

In yet another aspect of the system, the target nerve can emanate from the sacral plexus. For instance, the target nerve can be the posterior tibial nerve.

In still another aspect of the system, the first electrode can have a skin-contacting surface having an area of from about 0.75 mm$^2$ to about 2000 mm$^2$.

In one more embodiment, the electronic control system can be configured to deliver the first electrical nerve stimulation and the second electrical nerve stimulation at a current of about 0.1 milliamps, where the electronic control system can be further configured to incrementally increase the current until the baseline current and the threshold current are determined.

In an additional embodiment, the electronic control system can be configured to deliver the first electrical nerve stimulation and the second electrical nerve stimulation at a voltage of about 0.1 volts, where the voltage is incrementally increased until the baseline voltage and the threshold voltage are determined.

In still another embodiment, the electronic control system can be configured to deliver the first electrical nerve stimulation and the second electrical nerve stimulation at a frequency ranging from about 0.1 Hertz to about 50 Hertz.

In one more aspect of the system, the medical condition can be a urinary disorder, a bowel disorder, or a sexual disorder. For instance, the urinary disorder can be overactive bladder, urge incontinence, or stress incontinence, or a combination thereof; the bowel disorder can be bowel incontinence or irritable bowel syndrome; and the sexual disorder can be erectile dysfunction, detrusor over-activity, or persistent sexual arousal syndrome.

In a further aspect, the system can be portable.

In yet another aspect, disclosed is a method for treating a medical condition in a subject by transcutaneously delivering electrical nerve stimulation to the subject to stimulate a target nerve. The method includes positioning a first electrode adjacent to a surface of non-glabrous skin, wherein the first electrode is a cathode; positioning a second electrode adjacent to a surface of non-glabrous or glabrous skin, where in the second electrode is a ground electrode spaced apart a predetermined distance from the first electrode; and transcutaneously delivering a first electrical nerve stimulation to the target nerve via the first electrode and the second electrode.

In one particular aspect of the method, the non-glabrous skin can be located at a first ankle of the subject proximate a first medial malleolus and at least partly overlies a first flexor retinaculum. Further, the non-glabrous skin can at least partly overlie a cephalic border of the first flexor retinaculum.

In another aspect, the method can further include positioning a compressive device over the first electrode to immobilize the target nerve.

In one more aspect of the method, the target nerve can emanate from the sacral plexus. For instance, the target nerve can be the posterior tibial nerve.

In an additional aspect of the method, the first electrode can have a skin-contacting surface having an area of from about 0.75 mm$^2$ to about 2000 mm$^2$.

In another embodiment of the method, the first electrical nerve stimulation can be delivered at a current of less than about 50 milliAmps. Further, the current can be delivered as a series of square-wave pulses, wherein each pulse has a duration of less than about 400 microseconds.

In one more embodiment of the method, the first electrical nerve stimulation can be delivered at a voltage of less than about 300 volts. Further, the voltage can be delivered as a series of square wave pulses, wherein each pulse has a duration of less than about 400 microseconds.

In an additional embodiment of the method, the first electrical nerve stimulation can be delivered at a frequency ranging from about 0.1 Hertz to about 50 Hertz.

In one more aspect, the method can include one or more treatment sessions, wherein the one or more treatment sessions can each have a duration of about 1 hour or less. Further, the treatment sessions can be administered multiple times per day, week, month, or year.

In one particular embodiment, the method can further include stimulating a second target nerve, where the method includes: positioning a third electrode adjacent to a surface of non-glabrous skin, wherein the third electrode is a cathode; positioning a fourth electrode adjacent to a surface of non-glabrous or glabrous skin, wherein the fourth electrode is a ground electrode spaced apart a predetermined distance from the third electrode, wherein the fourth electrode is an anode; and transcutaneously delivering a second electrical nerve stimulation to the second target nerve through the third electrode.

In one aspect, the non-glabrous skin can be located at a second ankle of the subject proximate a second medial malleolus and can at least partly overlie a second flexor retinaculum. Further, the non-glabrous skin can at least partly overlie a cephalic border of the second flexor retinaculum.

In one particular aspect of the method, the second electrical nerve stimulation can be delivered simultaneously with the first electrical nerve stimulation.

In another aspect of the method, the second electrical nerve stimulation can be delivered out of phase with the first electrical nerve stimulation.

In yet another aspect, the method can include one or more treatment sessions, where the one or more treatment sessions can each have a duration of about 30 minutes or less, such as when two electrical nerve stimulations are delivered.

In one embodiment of the method, the medical condition can be a urinary disorder, a bowel disorder, or a sexual disorder. For instance, the urinary disorder can be overactive bladder, urge incontinence, stress incontinence, or a combination thereof; the bowel disorder can be bowel incontinence or irritable bowel syndrome; and the sexual disorder can be erectile dysfunction, detrusor over-activity, or persistent sexual arousal syndrome.

In still another aspect, disclosed is a system configured to treat a medical condition in a subject by transcutaneously delivering electrical nerve stimulation to the subject to stimulate a first target nerve. The system includes a first electrode, wherein the first electrode is configured for placement on a non-glabrous skin surface, wherein the first electrode is a cathode; a second electrode, wherein the second electrode is configured for placement on a surface of non-glabrous or glabrous skin, wherein the second electrode is an anode; and an electronic control system coupled to the first electrode and the second electrode, wherein the electronic control system is configured to transcutaneously deliver a first electrical nerve stimulation to the first target nerve via the first electrode and the second electrode.

In one aspect of the system, the non-glabrous skin can be located at a first ankle of the subject proximate a first medial malleolus and can at least partly overlie a first flexor retinaculum. Further, the non-glabrous skin can at least partly overlie a cephalic border of the first flexor retinaculum.

In another aspect, the system can include a compressive device, where the compressive device is configured for placement over the first electrode to immobilize the first target nerve.

In one more aspect of the system, the first target nerve can emanate from the sacral plexus. For instance, the first target nerve can be the posterior tibial nerve.

In yet another aspect of the system, the first electrode can have a skin-contacting surface having an area of from about 0.75 mm$^2$ to about 2000 mm$^2$.

In one embodiment, the electronic control system can be configured to deliver the first electrical nerve stimulation at a current of less than about 50 milliAmps. Further, the electronic control system can be configured to deliver the current as a series of square-wave pulses, where each pulse has a duration of less than about 400 microseconds.

In another embodiment, the electronic control system can be configured to deliver the first electrical nerve stimulation at a voltage of less than about 300 volts. In addition, the electronic control system can be configured to deliver the voltage as a series of square-wave pulses, wherein each pulse has a duration of less than about 400 microseconds.

In still another embodiment, the electronic control system can be configured to deliver the first electrical nerve stimulation at a frequency ranging from about 0.1 Hertz to about 50 Hertz.

In one more aspect, the system can be configured to transcutaneously deliver electrical nerve stimulation to the subject to stimulate a second target nerve, where the system includes: a third electrode, where the third electrode is configured for placement on a non-glabrous skin surface, where the third electrode is a cathode; and a fourth electrode, where the fourth electrode is configured for placement on a non-glabrous or glabrous skin surface, where the fourth electrode is an anode, where the third electrode and the fourth electrode are coupled to the electronic control system; and where the electronic control system is configured to transcutaneously deliver a second electrical nerve stimulation to the second target nerve via the third electrode and fourth electrode.

In one aspect of the method, the non-glabrous skin can be located at a second ankle of a subject proximate a second medial malleolus and can at least partly overlie a second flexor retinaculum. Further, the non-glabrous skin can at least partly overlie a cephalic border of the second flexor retinaculum.

In yet another aspect, the electronic control system can be configured to deliver the second electrical nerve stimulation such that the second electrical nerve stimulation is out of phase with the first electrical nerve stimulation.

In one aspect of the system, the medical condition can be a urinary disorder, a bowel disorder, or a sexual disorder. For instance, the urinary disorder can be overactive bladder, urge incontinence, stress incontinence, or a combination thereof; the bowel disorder can be bowel incontinence or irritable bowel syndrome; and the sexual disorder can be erectile dysfunction, detrusor over-activity, or persistent sexual arousal syndrome.

In still another aspect, the system can be portable.

In one more aspect, disclosed is a band for transcutaneously delivering electrical nerve stimulation to a target nerve. The band has an outer-facing surface and a skin contacting surface and includes a tab located at a first end of the band; an anode disposed on the outer-facing surface and located at a second end of the band; a cathode disposed on the outer-facing surface between the tab and the anode; and a compression bead located on the outer facing surface between the tab and the cathode.

In one particular embodiment, an attachment means can be located on the outer-facing surface at the tab.

In another embodiment, the strap can be positioned on a release liner, where removal of the release liner exposes a skin-contacting adhesive on the skin-contacting surface.

In one more embodiment, the compression bead can be configured to apply a predetermined amount of pressure to the cathode to sufficiently immobilize the target nerve when the tab is folded over the cathode and attached to the outer-facing surface of the band between the cathode and the anode.

In another aspect, the skin-contacting surface can be configured for placement on a foot and ankle, where the cathode is positioned on a non-glabrous skin surface. Further, the non-glabrous skin can be proximate a medial malleolus and can at least partly overlies a flexor retinaculum. In addition, the non-glabrous skin at can least partly overlie a cephalic border of the flexor retinaculum. Also contemplated is a kit that includes a band for transcutaneously delivering electrical nerve stimulation to a target nerve. The band has an outer-facing surface and a skin contacting surface and includes a tab located at a first end of the band; an anode disposed on the outer-facing surface and located at a second end of the band; a cathode disposed on the outer-facing surface between the tab and the anode; and a compression bead located on the outer facing surface between the tab and the cathode.

In one embodiment, the kit can also include a cathode lead, a cathode connector, an anode lead, and an anode connector, where a head of the cathode can be configured to receive the cathode connector and a head of the anode can be configured to receive the anode connector.

In an additional aspect, disclosed is a brace for transcutaneously delivering electrical nerve stimulation to a target nerve. The brace includes an ankle portion for encircling an ankle of a subject, wherein the ankle portion is configured to allow for formation of an opening in the ankle portion proximate a medial malleolus; a compressive strap configured to wrap around the ankle portion, wherein the compressive strap is configured to apply a predetermined amount of pressure to the cathode to sufficiently immobilize the target nerve; and a foot portion for encircling a foot of a subject, wherein the foot portion includes a cut-out section, wherein the cut-out section exposes an arch of the foot when the brace is placed on the foot.

In one embodiment of the brace, the opening can at least partly overlie a flexor retinaculum. Further, the opening can at least partly overlie a cephalic border of the flexor retinaculum.

In an additional embodiment, the brace can further include a pre-perforated dot matrix including one or more removable dots, where the opening is formed by removal of one of the dots.

In one aspect of the brace, the opening can be configured to permit exposure of a cathode positioned on the non-glabrous skin surface.

In another aspect of the brace, the cut-out section can be configured to permit placement of an anode at the arch of the foot.

Also contemplated is a kit that can include a brace for transcutaneously delivering electrical nerve stimulation to a target nerve. The brace includes an ankle portion for encircling an ankle of a subject, wherein the ankle portion is configured to allow for formation of an opening in the ankle portion proximate a medial malleolus; a compressive strap configured to wrap around the ankle portion, wherein the compressive strap is configured to apply a predetermined amount of pressure to the cathode to sufficiently immobilize the target nerve; and a foot portion for encircling a foot of a subject, wherein the foot portion includes a cut-out section, wherein the cut-out section exposes an arch of the foot when the brace is placed on the foot.

In one embodiment, the kit can further include a cathode, an anode, a cathode lead, a cathode connector, an anode lead, and an anode connector, where a head of the cathode can be configured to receive the cathode connector and a head of the anode can be configured to receive the anode connector.

These and other aspects of the present disclosure will become apparent upon reference to the following detailed description.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

DEFINITIONS

Figure 1:
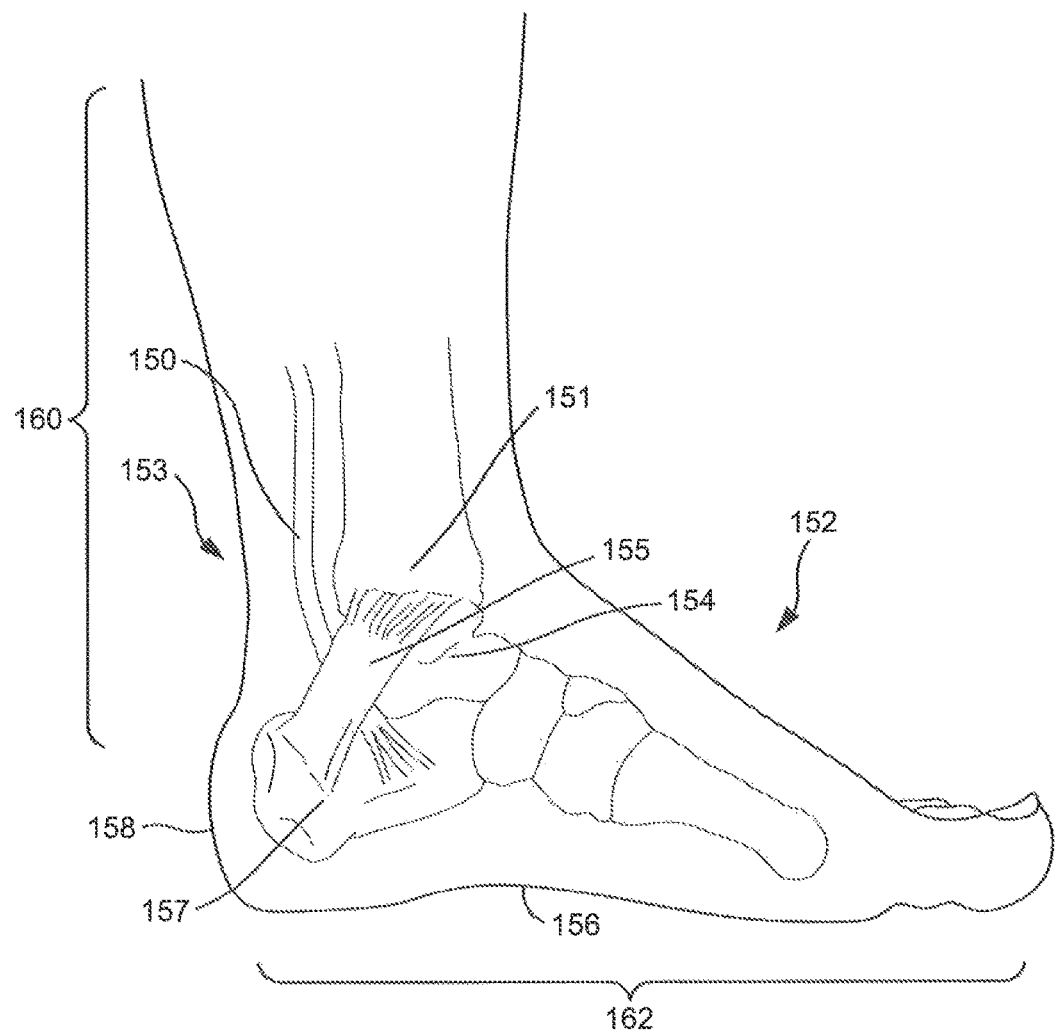
FIG. 1 is a side view of a leg and foot showing the disposition of the posterior tibial nerve underneath the flexor retinaculum at a location proximate the medial malleolus, where such location can serve as placement of the cathode of the present invention.

As used herein, the term "carrier frequency refers to a waveform that has a fixed center frequency that has been modulated (i.e., altered) in a way that its amplitude, frequency, phase or some other property varies. The frequency is measured in Hertz (cycles per second). For purposes of the present invention, a carrier frequency can be selected to provide low skin impedance and to carry a modulating frequency. Desirably, a carrier frequency is a high frequency waveform.

As used herein, the term "disposable" refers to a product that is so inexpensive that it may economically be discarded after only a single use. Products that are "disposable" are typically intended for single use. The term "single-use" refers to a product that is intended to be used only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse. As desired, the cathodes and anodes of the present disclosure may be disposable.

As used herein, the term "glabrous skin" refers to smooth skin having a surface without hairs or projections or skin that is normally devoid of hair. For instance, it is found on the ventral portion of the fingers, the palmar surfaces of the hands, and the soles of the feet. Meanwhile, the term "non-glabrous skin" refers to skin having a surface that normally includes hair and sebaceous glands.

As used herein, the term "intact skin" refers to skin that is sound, unbroken and uninjured, or not altered in any meaningful way such as, for example, by fresh surgical incision, fresh piercing by an instrument such as a needle, trocar or the like.

As used herein, the terms "painful response" or "painful sensation" refer to a highly disagreeable sensation generated by the activation of sensory nociceptors. Nociception describes the perception of acute pain.

As used herein, the term "subjects" refers to "mammals," where these terms are used broadly to describe organisms which are within the class mammalia, including the orders carnivore (e.g., dogs and cats), and primates (e.g., humans, chimpanzees, and monkeys). While humans are referred to in many embodiments of the disclosure, other mammals may benefit from the method of the present disclosure with minor modifications.

DETAILED DESCRIPTION

Reference now will be made in detail to various embodiments of the disclosure, one or more examples of which are set forth below. Each example is provided by way of explanation, not limitation of the disclosure. In fact, it will be apparent to those skilled in the art that various modifications and variations may be made in the present disclosure without departing from the scope or spirit of the invention. For instance, features illustrated or described as part of one embodiment, may be used on another embodiment to yield a still further embodiment. Thus, it is intended that the present invention cover such modifications and variations.

In one embodiment, the present disclosure is directed to a system and method for transcutaneously (i.e., non-invasively via intact skin) monitoring a medical condition (e.g., urinary, bowel, and sexual disorders) in a subject, where improvement or lack thereof in the medical condition can be determined by comparing a baseline current or voltage to a later-measured threshold current or voltage at which a sensory response or motor response is elicited. Improvement in the medical condition can correspond with a decrease in the threshold current or voltage at which a sensory response or motor response is elicited as compared to the baseline current at which a sensory response or motor response was previously elicited. Further, in another embodiment and either separately or subsequent to the aforementioned monitoring of a medical condition such as a bladder disorder, bowel disorder, or sexual disorder, the present inventors have found that transcutaneous stimulation of the posterior tibial nerve can also be used to treat such a medical condition. Both monitoring and treatment can be carried out in a non-invasive manner substantially free of a painful sensation or painful response via electrical nerve stimulation of a target nerve, despite stimulation through non-glabrous skin. The stimulation is delivered from an electrode placed on a non-glabrous skin surface, where the electrode placement sufficiently immobilizes the target nerve with adequate pressure such that the stimulation is effective and can be carried out in a controlled manner. In particular, the cathode can be positioned adjacent to a surface of non-glabrous skin. In one embodiment, the surface of non-glabrous skin can be on a subject's ankle proximate the medial malleolus and can at least partly overlie the flexor retinaculum, such as at its cephalic border. The present inventors have found that the combination of the cathode placement site and the pressure applied to the surface of the skin through the cathode can sufficiently immobilize the posterior tibial nerve. Also contemplated by the present disclosure are various electrode bands and braces to ensure accurate electrode placement and target nerve immobilization, as well as kits for the monitoring and treatment of the medical condition including electrodes, leads, connectors, etc.

Turning to FIG. 1, the anatomy of the area of the foot and ankle through which nerve stimulation can be applied to the posterior tibial nerve is shown. The posterior tibial nerve 150 runs along a subject's leg near the tibia 151 and ankle 153 near the medial malleolus 154. As discussed in more detail below, the present inventors have found that the posterior tibial nerve 150 can be transcutaneously stimulated via a cathode placed adjacent to a surface of non-glabrous skin, such as a surface of non-glabrous skin proximate the medial malleolus 154 and at least partly overlying the flexor retinaculum 155, without eliciting a painful response or painful sensation, despite the skin around the medial malleolus 154 being non-glabrous. In one particular embodiment, the non-glabrous skin to which the cathode is applied can at least partly overlie a cephalic border of the flexor retinaculum 155. Further, the present inventors have found that the combination of the flexor retinaculum 155 holding or binding down the posterior tibia nerve 150 and the placement of the cathode such that it at least partly overlies the cephalic border of the flexor retinaculum 155 can provide sufficient pressure to effectively immobilize and stimulate the posterior tibial nerve 150 at that location. However, it is also to be understood that the cathode can be placed adjacent any area of non-glabrous skin 160 as shown in FIG. 1 so long as the cathode and other components of the electrical nerve stimulation system utilized can sufficiently immobilize the target nerve (e.g., the posterior tibial nerve) at the stimulation site. Thus, unlike other systems and methods described previously, with the monitoring and treatment systems and methods of the present disclosure, it is not necessary to place the cathode on a glabrous skin surface 162 such as the bottom of the foot near the arch 156 or heal 158, where such placement is cumbersome and limits the mobility of the subject being treated. Various embodiments of the monitoring and treatment systems and methods of the present disclosure, along with the various electrodes and kits that can be utilized in conjunction with the monitoring and treatment systems and methods, are discussed in more detail below.

System and Method for Monitoring of a Medical Condition

Figure 2:
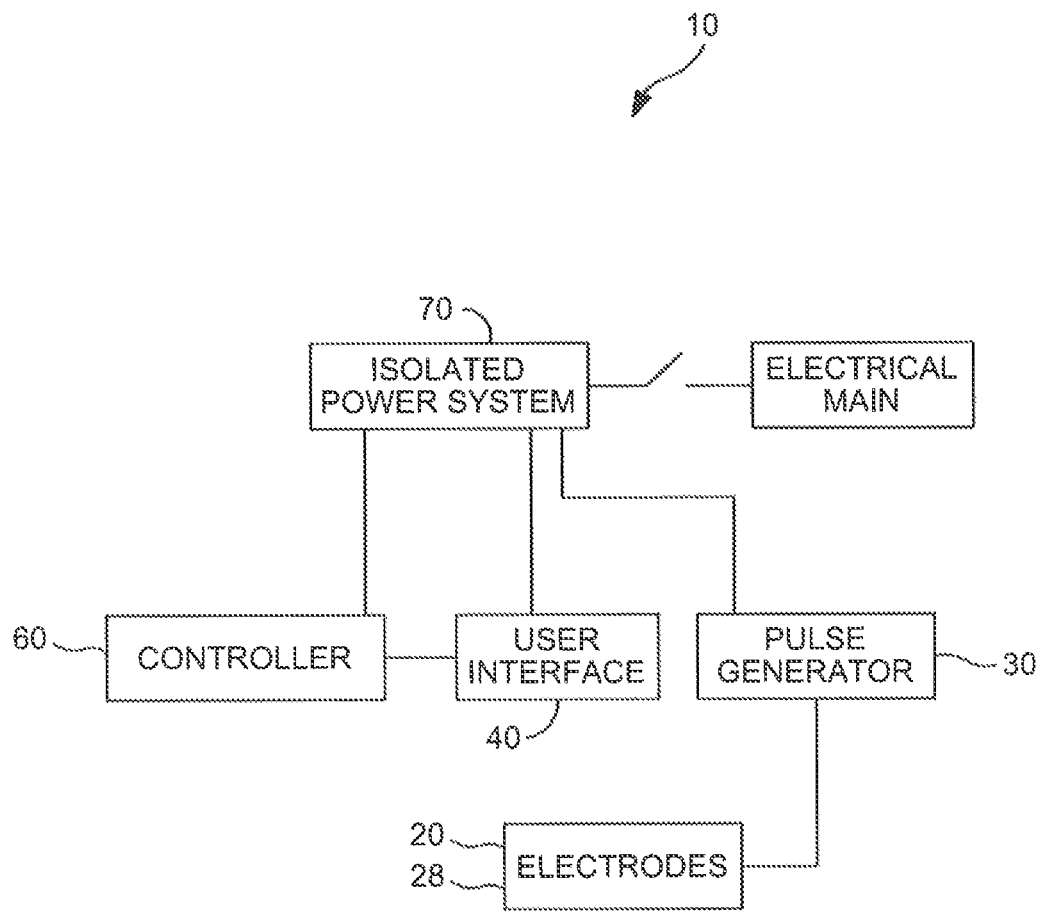
FIG. 2 is a schematic diagram of one embodiment of a system for transcutaneously stimulating a target nerve in accordance with the present disclosure.

In one embodiment, a method and system of the present disclosure contemplates non-invasively monitoring a medical condition via transcutaneous electrical nerve stimulation of a target nerve. The medical condition can be a bladder disorder such as overactive bladder, urge incontinence, or stress incontinence, a bowel disorder such as bowel incontinence or irritable bowel syndrome, or a sexual disorder. The target nerve that can be stimulated to monitor the medical condition can emanate from the sacral plexus. For instance, the target nerve can be the posterior tibial nerve 150 discussed above with reference to FIG. 1. As shown in FIG. 2, the system 10 used for such monitoring may include electrodes (cathode 20 and anode 28), a pulse generator 30, a user interface 40, an electronic control system 60, and an isolated power system 70. While an experimental-scale system is shown and described, it is contemplated that a more compact unit could be used to control and deliver the desired electrical stimulation. Further, in some embodiments, the system can be portable and user-friendly such that a subject can utilize the system at home, outside of a medical office setting. However, it is also to be understood that the system can be used in a medical office setting. In addition, it is contemplated that one or more subjects can be monitored and/or treated from a main system 10, where each subject is connected to a separate electrode ensemble.

The cathode 20 can have a diameter of from about 1 millimeter (mm) to about 50 mm, such as from about 1.25 mm to about 37.5 mm, such as from about 1.5 mm to about 18.75 mm. As such, the cathode 20 can each have a skin-contacting surface area that is from about 0.75 mm$^2$ to about 2000 mm$^2$, such as from about 1.25 mm$^2$ to about 1125 mm$^2$, such as from about 1.75 mm$^2$ to about 275 mm$^2$.

Meanwhile, like the cathode, the anode 28 can have a diameter of from about 1 millimeter (mm) to about 50 mm, such as from about 1.25 mm to about 37.5mm, such as from about 1.5 mm to about 18.75 mm. As such, the anode 28 can also have a skin-contacting surface area that is from about 0.75 mm$^2$ to about 2000 mm$^2$, such as from about 1.25 mm$^2$ to about 1125 mm$^2$, such as from about 1.75 mm$^2$ to about 275 mm$^2$. While not bound to a particular theory of operation, it is generally believed that by using a stimulating electrode on the surface of the skin that is substantially smaller than typical skin-contacting stimulating electrodes, the amount of current or voltage needed to stimulate a nerve or nerve fiber can be reduced. Various embodiments of the electrodes and how the electrodes are attached to the desired location on a subject's skin are discussed in more detail below in reference to the electrode band and brace contemplated by the present disclosure.

In one aspect, the electrodes (cathode 20 and anode 28) may be electrically connected via cathode lead 101 and anode lead 105, respectively, (see, e.g. FIGS. 3-4 and 11) to a pulse generator 30. The pulse generator 30 can be a constant-current stimulator. One exemplary stimulator is the constant-current DIGITIMER DS5 peripheral electrical stimulator available from Digitimer Ltd., England. The DIGITIMER DS5 machine delivers a bipolar stimulation via a pair of electrodes (cathode 20 and anode 28), where both electrodes are within a specified distance from the target nerve. In another aspect of the present disclosure, pulse generator 30 may be a constant-voltage pulse-generator. For example, three such generators are available from Grass Technologies, a subsidiary of Astro-Med, Inc., RI, US, as models S88X, S48, SD9. It should also be understood that monopolar stimulation, where just one electrode is placed within a specified distance from the target nerve and a reference electrode is located elsewhere, will also activate a target nerve and cause muscle contraction, but with lesser effectiveness.

The system 10 also includes a user interface 40, which is a computer that can operate software designed to record signals passed from the electronic control system 60, and to drive the electronic control system's output from the pulse generator 30. Possible software includes Cambridge Electronic Design's (UK) "SPIKE" program. The software is programmable and can record and analyze electrophysiological signals, as well as direct the electronic control system to enable electrical nerve stimulation for monitoring and/or treatment of a medical condition.

Further, the electronic control system 60 performs data acquisition functions by acquiring electrophysiological waveform data from, for instance, signal amplifiers/conditioners (not shown), and outputs electrical signals for real-time control of the pulse generator 30. The electronic control system 60 may have onboard memory to facilitate high speed data capture, independent waveform sample rates and on-line analysis. In one aspect, the electronic control system 60 may be a POWER 1401 data-acquisition interface unit available from Cambridge Electronic Design, UK.

The various components of the system 10 can be powered by an isolated power supply or system 70 to protect them from ground faults and power spikes carried by the electrical main. An exemplary isolated power system is Model IPS115 Isolated Medical-grade Power System from Grass Technologies, a subsidiary of Astro-Med, Inc., West Warwick, R.I., USA.

Generally, the target nerve (e.g., posterior tibial nerve 150) can be stimulated through placement of a stimulation electrode (e.g., cathode 20) on a non-glabrous skin surface 160, such as a surface of non-glabrous skin proximate the medial malleolus 154 and at least partly overlying the flexor retinaculum 155 (see FIG. 1). As shown in FIG. 1, the posterior tibial nerve 150 is bound down by the flexor retinaculum 155, so placement of the cathode 20 on an area of skin at least partly overlying a cephalic border of the flexor retinaculum 155 can help ensure proper and consistent placement of the cathode 20 for effective stimulation. The pressure at which the cathode 20 is applied to the skin can also be controlled and measured to ensure that a consistent amount of pressure is used for each stimulation to ensure accurate results for comparison. In one embodiment, the cathode 20 can be placed on a non-glabrous skin surface 160 at a location that is about 0.1 centimeters to about 8 centimeters (e.g., about 5 centimeters) posterior to the medial malleolus and posterior to the tibia 151 to ensure that the cathode 20 is placed on a non-glabrous skin surface 160 that at least partly overlies the flexor retinaculum 155, such as at its cephalic border. Further, in a bipolar configuration, the ground electrode (e.g., anode 28) can be placed on a glabrous skin surface 162 or a non-glabrous skin surface 160 that can be located a distance of about 10 centimeters (cm) or less away from the cathode 20. For instance, the distance between the cathode 20 and the anode 28 can range from about 1 centimeter (cm) to about 10 cm, such as from about 2 cm to about 9 cm, such as from about 3 cm to about 8 cm. In addition, during stimulation, a compressive device such as a gel compression bead or strap (discussed in more detail below) can be placed over the cathode to ensure sufficient immobilization of the target nerve via the application of adequate pressure so that the stimulation can be effectively and consistently applied, which enables an accurate comparison of the subject's threshold intensity to a baseline intensity to monitor the subject for a medical condition, as explained below.

For instance, to monitor a subject having a medical condition, a low level of stimulation can be applied to the target nerve via the cathode, and the stimulation intensity (current or voltage) can be incrementally increased until a sensory response or motor response is observed in the patient. If the stimulation intensity is in the form of a current, the initial current applied can be about 0.1 milliamps (mA), and the current applied can be gradually and incrementally increased until a sensory response or motor response is elicited. Meanwhile, if the stimulation intensity is in the form of a voltage, the initial voltage applied can be about 0.1 volts, and the voltage applied can be gradually and incrementally increased until a sensory response or a motor response is elicited. It should be understood that a sensory response is distinguished from a motor response in that a sensory response is characterized by a tingling sensation in the subject, while a motor response is observed as a visible twitch. Generally, a motor response can be elicited at an intensity (e.g., current or voltage) that is about 3 times to about 4 times the intensity at which a sensory response can be elicited. The stimulation intensity (e.g., current or voltage) at which the sensory response or motor response is elicited in the subject is then recorded, and this threshold intensity can be compared to a baseline intensity, where the baseline intensity is the intensity at which a sensory response or motor response was previously elicited in a subject suffering from the medical condition (e.g., overactive bladder, urge incontinence, stress incontinence, bowel incontinence, irritable bowel syndrome, sexual disorder, or a combination thereof, etc.), such as prior to any treatment or intervention or when the condition was initially diagnosed.

In general, if the stimulation is in the form of a current, the baseline current at which a sensory response can be typically elicited in an able-bodied subject not suffering from the medical condition can be about 5 milliamps (mA) or less. For instance, the baseline current can range from about 0.1 mA to about 5 mA, such as from about 0.25 mA to about 4 mA, such as from about 0.5 mA to about 3 mA. Meanwhile, the baseline current at which a sensory response can be elicited in a subject suffering from the medical condition can be about 25 milliamps or less. In one embodiment, the baseline current can be at least about 6 mA. For example, the baseline current can range from about 6 mA to about 25 mA, such as from about 7 mA to about 20 mA, such as from about 8 mA to about 15 mA. On the other hand, the baseline current at which a motor response can be typically elicited in an able-bodied subject not suffering from the medical condition can be about 20 milliamps (mA) or less. For instance, the baseline current can range from about 0.3 mA to about 15 mA, such as from about 0.75 mA to about 12 mA, such as from about 1.5 mA to about 9 mA. Meanwhile, the baseline current at which a motor response can be elicited in a subject suffering from the medical condition can be about 50 milliamps or less. In one embodiment, the baseline current can be at least about 18 mA. For example, the baseline current can range from about 18 mA to about 37.5 mA, such as from about 21 mA to about 30 mA, such as from about 24 mA to about 27 mA. Such initial baseline currents can be monitored over time, and additional currents (i.e., threshold currents) at which a sensory response or motor response is elicited in the subject can be measured. Generally, a decrease in the threshold current to elicit a sensory response or motor response as compared to the baseline current to elicit a sensory response or motor response indicates that the medical condition has improved. It is to be understood that the baseline current is the current required to elicit a sensory response or a motor response prior to an electrical nerve stimulation treatment session or any other type of therapy (pharmacological, surgical, exercise etc.) used to treat the medical condition being monitored, and the threshold current is the current required to elicit a sensory response or a motor response after the passage of any amount of time or after an electrical nerve stimulation treatment session or any other type of therapy (pharmacological, surgical, exercise etc.) used to treat the medical condition being monitored.

Further, if the stimulation is in the form of a voltage, the baseline voltage at which a sensory response can be typically elicited in an able-bodied subject not suffering from the medical condition can be about 30 volts or less. For instance, the baseline voltage can range from about 1 volt to about 30 volts, such as from about 1.5 volts to about 25 volts, such as from about 3 volts to about 10 volts. Meanwhile, the baseline voltage at which a sensory response can be elicited in a subject suffering from the medical condition can be about 150 volts or less. In one embodiment, the baseline voltage can be at least about 25 volts. For example, the baseline voltage can range from about 25 volts to about 150 volts, such as from about 35 volts to about 120 volts, such as from about 50 volts to about 100 volts. On the other hand, the baseline voltage at which a motor response is typically elicited in an able-bodied subject not suffering from the medical condition can be about 120 volts or less. For instance, the baseline voltage can range from about 3 volts to about 100 volts, such as from about 4.5 volts to about 75 volts, such as from about 25 volts to about 65 volts. Meanwhile, the baseline voltage at which a motor response can be elicited in a subject suffering from the medical condition can be about 300 volts or less. In one embodiment, the baseline voltage can be at least about 100 volts. For example, the baseline voltage can range from about 100 volts to about 300 volts, such as from about 125 volts to about 250 volts, such as from about 150 volts to about 200 volts. Such initial baseline voltages can be monitored over time, and additional voltages (i.e., threshold voltages) at which a sensory response or motor response is elicited in the subject can be measured. Generally, a decrease in the threshold voltage to elicit a sensory response or motor response as compared to the baseline voltage to elicit a sensory response or motor response indicates that the medical condition has improved. It is to be understood that the baseline voltage is the voltage required to elicit a sensory response or a motor response prior to an electrical nerve stimulation treatment session or any other type of therapy (pharmacological, surgical, exercise etc.) used to treat the medical condition being monitored, and the threshold voltage is the voltage required to elicit a sensory response or a motor response after the passage of any amount of time or after an electrical nerve stimulation treatment session or any other type of therapy (pharmacological, surgical, exercise etc.) used to treat the medical condition being monitored.

Typically, the stimulation frequency for the monitoring of a medical condition via stimulation of the posterior tibial nerve as discussed above can range from about 0.1 Hertz to about 50 Hertz, such as from about 0.5 Hertz to about 40 Hertz, such as from about 1 Hertz to about 30 Hertz, such as from about 5 Hertz to about 20 Hertz. Such stimulation frequencies can be utilized without causing painful sensations to a subject even when the electrodes are placed on non-glabrous skin, which, without intending to be limited by any particular theory, can be due in part to the small dimensions of the electrodes discussed above as well as the location at which the electrodes are applied.

Although not required, in addition to a stimulation (modulating) frequency, an optional carrier frequency can be utilized to improve energy transfer through the skin. The U.S. Food and Drug Administration recommends that power calculations for transcutaneous stimulation use a skin impedance of about 500 Ω. Studies show that the use of carrier frequencies up to 1 MHz can reduce the skin's impedance to about 100 Ω. As such, in some embodiments, the carrier frequency can range from about 25,000 Hertz to about 500,000 Hertz, such as from about 50,000 Hertz to about 300,000 Hertz, such as from about 100,000 Hertz to about 200,000 Hertz.

In addition to monitoring a subject with a medical condition as discussed above, the same system 10 can be utilized for the treatment of the medical condition, after which the monitoring method discussed above can be repeated after one or more treatment sessions to determine if the threshold intensity at which a sensory response or motor response is elicited in the subject has decreased compared to a baseline intensity, indicating that the treatment is effective at improving, alleviating, or curing the medical condition.

System and Method for Treatment of a Medical Condition

Thus, in additional embodiments, a method and system of the present disclosure provides for transcutaneous, non-invasive treatment of a medical condition via electrical nerve stimulation of a target nerve. The medical condition can be a urinary disorder, a bowel disorder, or sexual disorder, and the target nerve that can be stimulated to treat such medical conditions. For instance, the target nerve can be the posterior tibial nerve. Such a system and method can include the components shown in FIG. 1 and discussed above in reference to a system and method for treating a medical condition.

The disclosed method and system provides great freedom to those suffering from overactive bladder or urinary incontinence, allowing them to sleep through the night, shop, golf, enjoy a movie, drive long distances, and many other activities, without the urgent need to urinate. The disclosed method and system can also alleviate symptoms for other medical conditions such as bowel disorders and sexual disorders.

In representative embodiments, the method and system can be used in the treatment of a medical condition. By treatment it is meant that at least an alleviation or reduction of the symptoms associated with the medical condition afflicting the subject. However, treatment also includes situations where the medical condition, or at least symptoms associated therewith, are completely inhibited, e.g. prevented from happening, or stopped, e.g. terminated, such that the subject no longer suffers from the symptoms that characterize the medical condition.

Generally, the target nerve (e.g., posterior tibial nerve) can be stimulated through placement of a stimulation electrode (e.g., cathode 20) adjacent a non-glabrous skin surface 160, such as a skin surface proximate the medial malleolus 154 and at least partly overlying the flexor retinaculum 155, such as at its cephalic border, while the ground electrode (e.g., anode 28) can be placed on a glabrous skin surface 162 or a non-glabrous skin surface 160 that can be located a distance of about 10 centimeters (cm) or less away from the cathode 20. For instance, the distance between the cathode 20 and the anode 28 can range from about 1 centimeter (cm) to about 10 cm, such as from about 2 cm to about 9 cm, such as from about 3 cm to about 8 cm. In addition, during stimulation, a compressive device such as a gel compression bead or strap (discussed in more detail below) can be placed over the cathode to ensure sufficient immobilization of the target nerve via the application of adequate pressure so that the stimulation can be effectively and consistently applied. In some embodiments, the stimulation can be applied proximate the medial malleolus on one ankle of the subject to stimulate a first target nerve, although it is also contemplated that stimulation can be applied proximate to the medial malleolus on the subject's other ankle as well to stimulate a second target nerve. Such bilateral stimulation can allow for more efficient treatment of a subject at each treatment session, as discussed in more detail below. In reference to FIG. 19, such bilateral stimulation involves the use of both of a subject's feet 152a and 152b, where a first cathode 20a is positioned adjacent a surface of non-glabrous skin, such as where the skin is proximate a first medial malleolus 154a and at least partly overlies a first flexor retinaculum 155a, such as at its cephalic border, and a first anode 28a is positioned adjacent a surface of glabrous or non-glabrous skin spaced apart a predetermined distance from the first cathode 20a, while a second cathode 20b is positioned adjacent a surface of non-glabrous skin, such as where the skin is proximate a second medial malleolus 154b and at least partly overlies the second flexor retinaculum 155b, such as at its cephalic border, and a second anode 28b is positioned adjacent a surface of glabrous or non-glabrous skin spaced apart a predetermined distance from the second cathode 20b.

Regardless of whether stimulation is being applied through one or more non-glabrous skin surfaces, such as skin that is proximate to one or both of a subject's medial malleoli, the stimulation frequency for treatment of a medical condition such as overactive bladder via stimulation of the posterior tibial nerve can range from about 0.1 Hertz to about 50 Hertz, such as from about 0.5 Hertz to about 40 Hertz, such as from about 1 Hertz to about 30 Hertz, such as from about 5 Hertz to about 20 Hertz. Such stimulation frequencies can be utilized without causing painful sensations to a subject even when the electrodes are placed on non-glabrous skin, which, without intending to be limited by any particular theory, is due in part to the small dimensions of the electrodes discussed above.

Further, the amount of stimulation current applied can be minimized at least because the current density is focused, which further avoids generating pain sensations. As such, the electrical nerve stimulation current of the present disclosure can be less than about 50 milliamps (mA), such as from about 0.1 mA to about 50 mA, such as from about 0.5 mA to about 25 mA, such as from about 1 mA to about 10 mA. Alternatively, the stimulation can be applied at a voltage that is less than about 300 volts. For instance, the voltage at which the electrical nerve stimulation can be applied can range from about 5 volts to about 300 volts, such as from about 10 volts to about 200 volts, such as from about 15 volts to about 150 volts, such as from about 20 volts to about 100 volts. In other words, in some embodiments, the stimulation current or voltage that is applied to treat the medical condition can be below that of the baseline current or voltage discussed above for monitoring a medical condition. In addition, after one or more treatments, the stimulation current can be reduced from a previous treatment session if it is determined that the medical condition has improved after carrying out the monitoring method discussed above.

Moreover, each stimulation pulse can have a duration of about 400 microseconds or less, such as from about 20 microseconds to about 400 microseconds, such as from about 40 microseconds to about 350 microseconds, such as from about 50 microseconds to about 300 microseconds. Moreover, it should be understood that in the case of bilateral electrical nerve stimulation, the electrical nerve stimulations can each have an interpulse interval that is the same as or greater than the duration of the other nerve stimulation to ensure that the stimulations do not overlap and interfere with each other, although it is also possible that the stimulations can be applied in phase with each other. If the stimulations are applied out of phase with each other, the stimulations can be delivered, for example, about 45° to about 270° out of phase, such as from about 90° to about 225° out of phase, such as from about 135° to about 180° out of phase.

Although not required, in addition to a stimulation (modulating) frequency, a carrier frequency can be utilized to improve energy transfer through the skin, so that modulating stimuli (current or voltage) can more easily and efficiently affect the target nerve. The U.S. Food and Drug Administration recommends that power calculations for transcutaneous stimulation use a skin impedance of 500 Ω. Studies show that the use of carrier frequencies up to 1 MHz can reduce the skin's impedance to 100 Ω. As such, in some embodiments, the carrier frequency can range from about 25,000 Hertz to about 500,000 Hertz, such as from about 50,000 Hertz to about 300,000 Hertz, such as from about 100,000 Hertz to about 200,000 Hertz.

For example, if the present invention utilizes an electrode having a diameter of approximately 2.5 mm (Area 0.05 cm$^2$ or A) to deliver electrical stimulation at 25 kHz (DC; square-wave) and 10 milliamps (Ipeak), then the power density (PD; Eqn. 1) used to deliver the same current (140 milliamps/cm$^2$) to the nerve is reduced by a factor of 5. The application of a carrier frequency would reduce the resulting power density from 500 mW/cm$^2$ to 100 mW/cm$^2$ if the same current density is applied to the nerve.

$$PD = ((I_{rms}^2 \times \Omega))/A \qquad \text{Eqn. 1:}$$

$$I_{rms} = I_{peak}(\sqrt{DC}) \qquad \text{Eqn. 2:}$$

Regardless of the particular stimulation intensity and frequency parameters utilized, the system of FIG. 2 can be used to provide electrical stimulation to a target nerve to treat a medical condition.

Generally, over the course of one or more treatment sessions, the threshold intensity (current or voltage) at which a sensory response or motor response is elicited in a subject undergoing treatment for the medical condition can be measured, as described in the monitoring method and system discussed above. With sufficient treatment, the threshold intensity will decrease compared to the baseline intensity, which corresponds with improvement or alleviation of the subject's symptoms from the medical condition. The treatment sessions when stimulation is applied proximate to one medial malleolus of a subject can each last from about 15 minutes to about 2 hours, such as from about 30 minutes to 1 hour, and can be once-weekly treatment sessions over about a 10 to 20 week period. In some embodiments, twelve one-hour treatment sessions can be administered over a twelve-week period. In still other embodiments, the treatment can be administered multiple times per day, week, month, or year. For instance, in one particular embodiment, the treatment can be administered more than one time per day, such as up to about 3 times per day. Further, if bilateral stimulation is used as opposed to stimulation through just one target nerve location subject, the duration of each treatment session can generally be cut in half while delivering the same amount of stimulation. Thus, if a treatment session where stimulation is delivered to one target nerve of a subject and lasts from about 30 minutes to about 1 hour, then a treatment session where stimulation is delivered bilaterally and proximate both medial malleoli of a subject can last from about 15 minutes to about 30 minutes. In any event, the electrical nerve stimulation discussed above can, over time, treat a subject's medical condition such as overactive bladder, urge incontinence, stress incontinence, bowel incontinence, irritable bowel syndrome, or sexual dysfunction.

Transcutaneous Electrical Nerve Stimulation Kits

Figure 3:
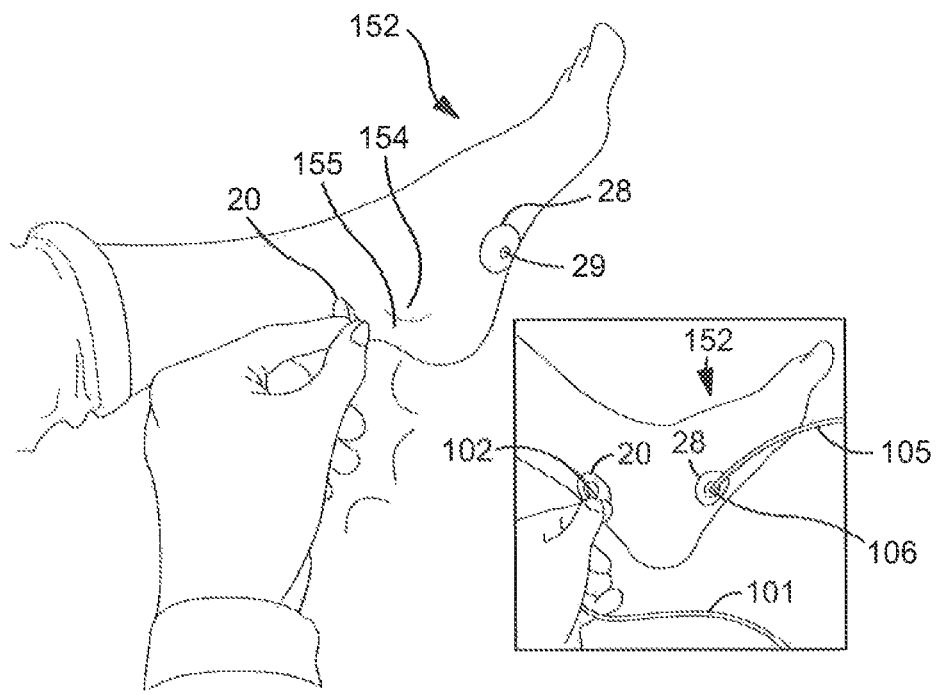
FIG. 3 shows one embodiment of a system for transcutaneously stimulating a target nerve in accordance with the present disclosure.
Figure 4:
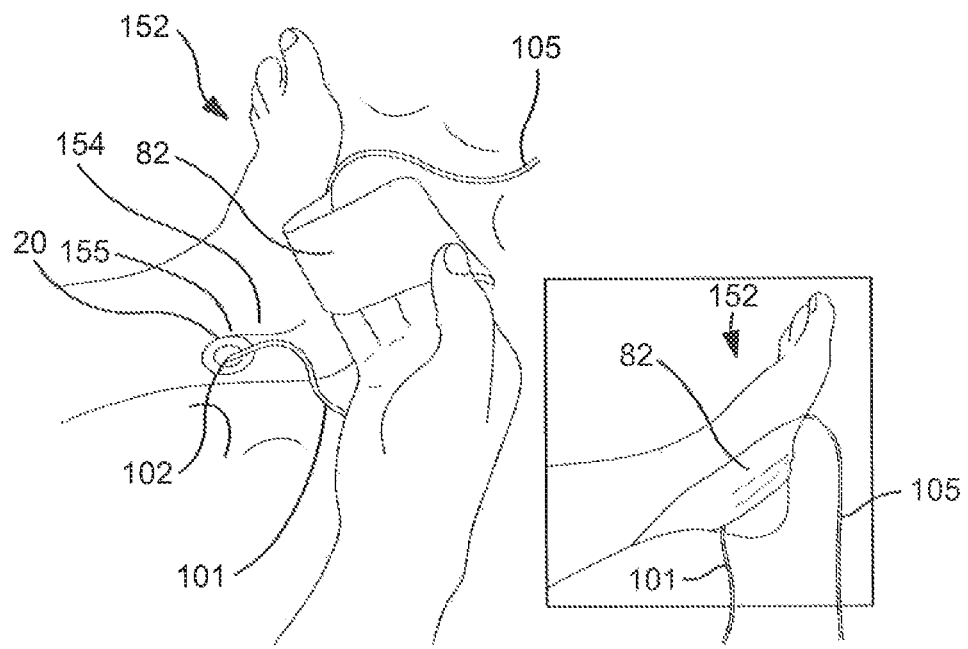
FIG. 4 shows another embodiment of a system for transcutaneously stimulating a target nerve in accordance with the present disclosure.

The methods described above for monitoring and/or treating a medical condition can be delivered to a subject via electrodes applied to a surface of the subject's skin and held in the proper location and position via a tape, wrap, brace, band, etc. Referring to FIG. 3, in one particular embodiment, a cathode 20 having a cathode head (not shown, see FIG. 7) can be positioned on a surface of non-glabrous skin proximate a subject's medial malleolus 154 and at least partly overlying the flexor retinaculum 155, such as at its cephalic border, while an anode 28 having an anode head (not shown, see FIG. 7) can be placed on a surface of glabrous or non-glabrous skin. For instance, the anode 28 can be placed on the foot 152 of the subject, such as at the arch 156 (see FIG. 1) of the foot 152. Next, a cathode lead 101 can be connected to the cathode head (not shown) via a cathode lead connector 102, and an anode lead 105 can be connected to the anode head (not shown) via an anode lead connector 106. The cathode lead 101 and the anode lead 105 can electrically connect the cathode 20 and the anode 28 to the electronic control system 10 discussed above so that a target nerve (i.e., the posterior tibial nerve 150) can be electrically stimulated by the electronic control system 10. As shown in FIG. 4, the combination of the design of the cathode lead connector 102 and the use of a tape or wrap 82 to provide sufficient pressure to the cathode 20 via compression ensures that the target nerve is sufficiently immobilized for accurate and effective electrical nerve stimulation. The tape or wrap 82 can also be placed over the anode 28 and anode lead connector 106 to ensure that the anode stays in place at, for example, the arch 156 of the foot 152.

Figure 5:
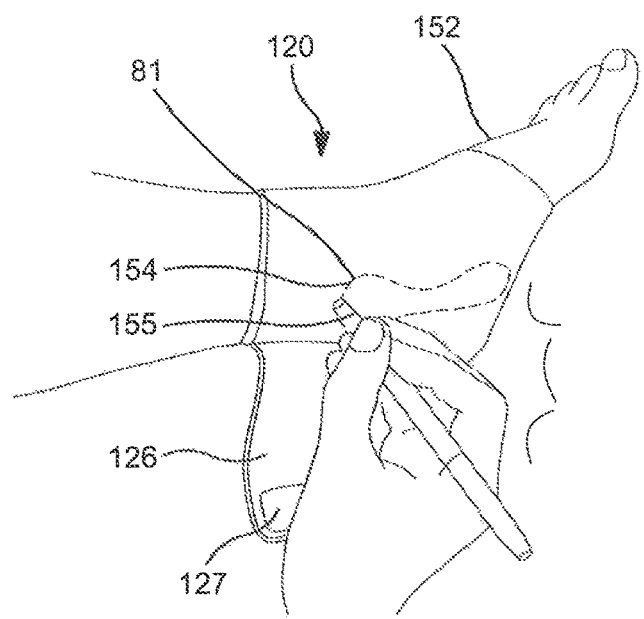
FIG. 5 shows one embodiment of a brace used for transcutaneously stimulating a target nerve in accordance with the present disclosure.
Figure 6:
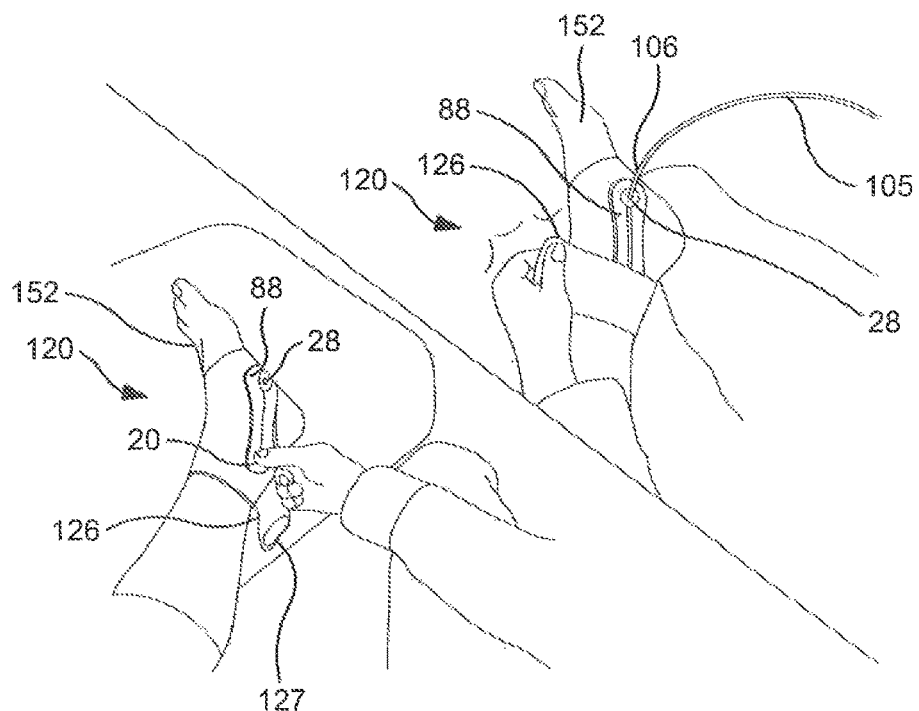
FIG. 6 shows the brace of FIG. 5 after an anode and cathode have been positioned over the brace in accordance with the present disclosure and after a compressive strap has been positioned around the cathode in accordance with the present disclosure.

In another embodiment, as shown in FIGS. 5 and 6, rather than using a tape or wrap to immobilize the target nerve at the cathode 20 and to ensure that the anode 28 is properly positioned, a brace 120 can be utilized. The brace 120 can be made from a soft material that can be comfortable, breathable, and non-irritating when in contact with a subject's skin and foot, such as cotton, wool, polyester, rayon, GORE-TEX, etc. The brace 120 can also include a cut out area 81 where material can be removed from the brace 120 so that an electrode band 88 can be disposed thereon. The cut out area 81 can be positioned on the brace 120 so that a cathode 20 on the electrode band 88 can be applied to a non-glabrous surface of skin proximate a subject's medial malleolus 154 and overlying the subject's flexor retinaculum 155, such as at its cephalic border, while the anode 28 can be applied to a glabrous or non-glabrous surface of skin, such as the subject's arch 156 of the subject's foot 152 (see FIG. 1). Such a configuration can allow for at home use by ensuring proper placement of the electrode band 88 due to the cut out area 81 in the brace 120. With the cut out area 81 formed, the foot 152 can slide into the brace 120, and an electrode band 88 can be applied to the subject's skin at the cut out area 81. Then, a cathode lead 101 (not shown, see FIG. 4) can be connected to the cathode 20 via a cathode connector 102 and an anode lead 105 can be connected to the anode 28 via an anode connector 106. Referring to FIGS. 5 and 6, the brace 120 can also include a compressive strap 126 and a compressive strap attachment means 127. The compressive strap 126 can wrap around the cathode 20 to apply a sufficient amount of pressure to immobilize the target nerve proximate the medial malleolus 154 at the flexor retinaculum 155, such as at its cephalic border, which allows for a consistent application of electrical nerve stimulation to the target nerve. Further, the attachment means 127 can ensure that the compressive strap 126 is secure such that the compressive strap 126 can maintain sufficient pressure through the cathode connector 102 and cathode 20 to immobilize the target nerve. The attachment means can include any suitable material for fastening the compressive strap 126 to the brace 120. For instance, the attachment means 127 can be a hook and loop type fastener such as a VELCRO™ fastener, a button, a snap, a hook, a pin, an adhesive, etc.

Figure 7:
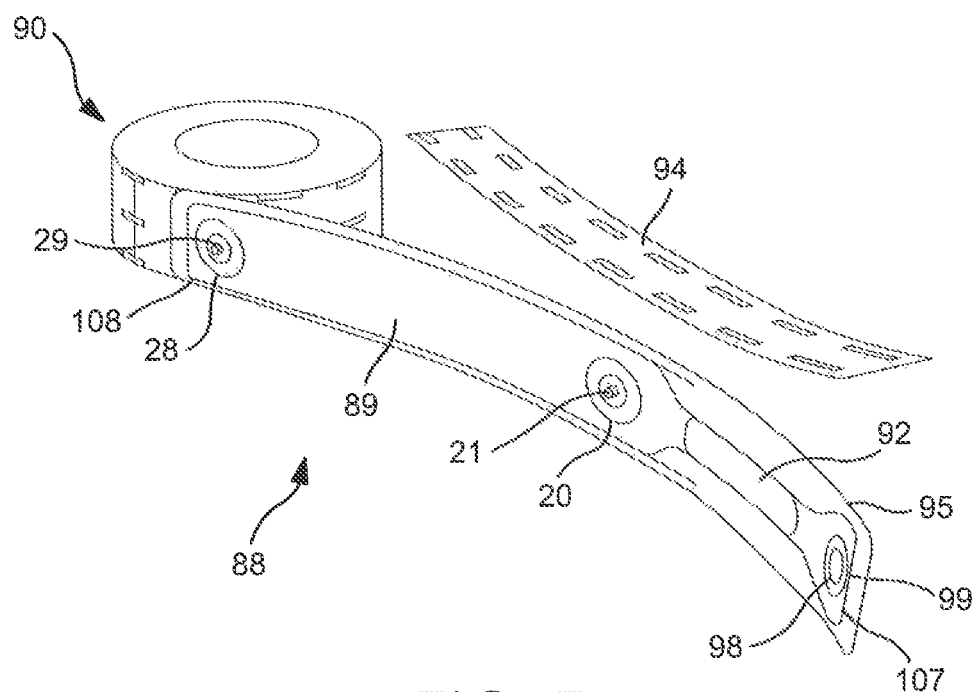
FIG. 7 shows one embodiment of a roll of disposable bands containing an anode and cathode used for transcutaneously stimulating a target nerve in accordance with the present disclosure.
Figures 8A, 8B:
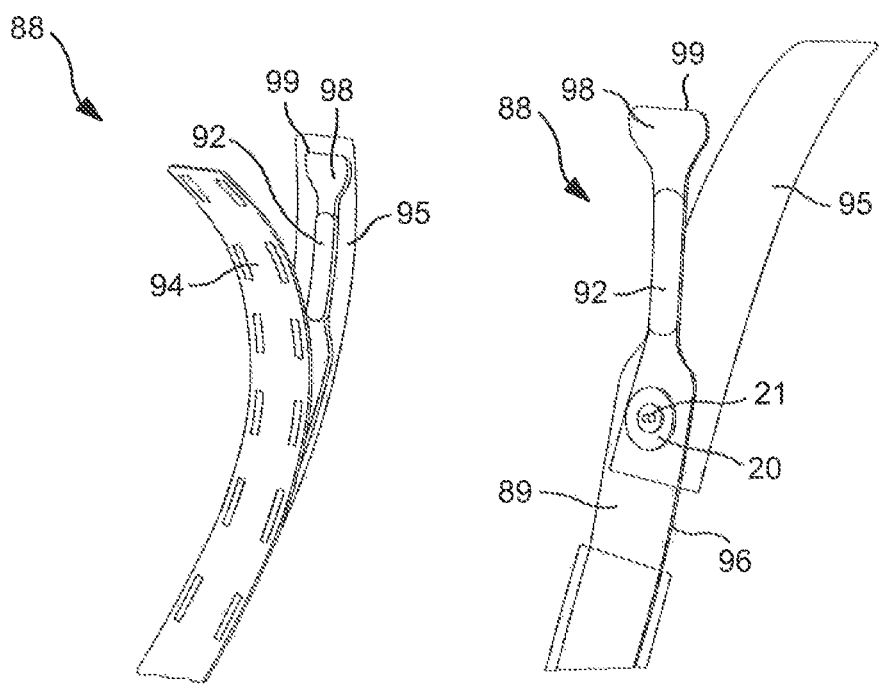
FIG. 8(a) shows a band from the roll of FIG. 7 before use and during removal of a first protective release liner in accordance with the present disclosure.
FIG. 8(b) shows a band from the roll of FIG. 7 after removal of the first protective release liner and during removal of the second protective release liner in accordance with the present disclosure.

In yet another embodiment, rather than utilizing an electrode band 88 in conjunction with a brace 120, an electrode band 88 can be utilized on its own to provide electrical nerve stimulation to a target nerve, as shown in FIGS. 7-11. Referring to FIG. 7, in one embodiment, an electrode band roll 90 can include multiple electrode bands 88. The electrode band roll 90 allows for a medical professional or the subject being monitored or treated with a convenient, easy manner in which to store and access the electrode bands 88, which are disposable. As shown in FIGS. 7, 8(a), and 8(b), each electrode band 88 can have an outer-facing surface 89 and a skin-contacting surface 96. The outer-facing surface 89 can include a tab 99 located at a first end 107 of the electrode band 88, an anode 28 located at a second end 108 of the electrode band 88, and a cathode 20 disposed between the tab 99 and the anode 28. The cathode 20 has a cathode head 21 and can be positioned on a surface of non-glabrous skin at a subject's medial malleolus, while an anode 28 having an anode head 29 can be placed on a surface of glabrous or non-glabrous skin in order to provide electrical nerve stimulation to a target nerve. Further, a gel compression bead 92 can be located on the outer-facing surface 89 between the tab 98 and the cathode 20. In addition, a tab attachment means 99 can be located on the tab 98, where the tab attachment means 99 can be a hook and loop type fastener such as a VELCRO™ fastener, a button, a snap, a hook, a pin, an adhesive, etc. Meanwhile, while on the electrode band roll 90, each electrode band 88 can be sandwiched between a first release liner 94 covering the outer-facing surface 89 and a second release liner 95 covering the skin-contacting surface 96 to protect each electrode band 88 until it is needed for use. When the first release liner 94 is removed, the outer-facing surface 89 of the electrode band 88 can be exposed such that a cathode lead 101 can be connected to the cathode 20 at cathode head 21 via a cathode connector 102 and an anode lead 105 can be connected to the anode 28 at anode head 29 via an anode connector 106 (see FIGS. 10-11). Further, when the second release liner 95 is removed, an adhesive on the skin-contacting surface 96 can be exposed so that the electrode band 88 can be adhered to a subject's skin at the desired location.

Figure 9:
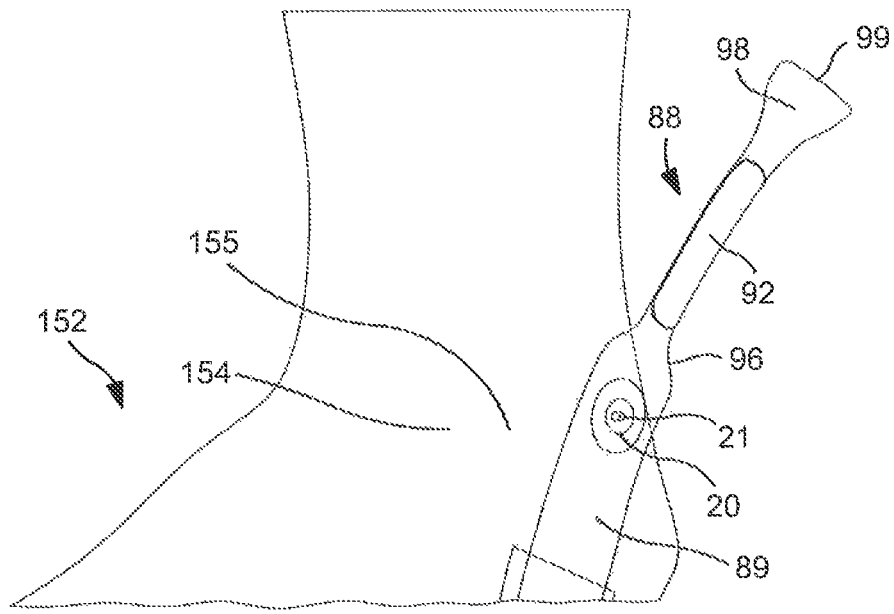
FIG. 9 shows application of a band for transcutaneously stimulating a target nerve to an area of skin proximate a subject's medial malleolus in accordance with one embodiment of the present disclosure.
Figure 10:
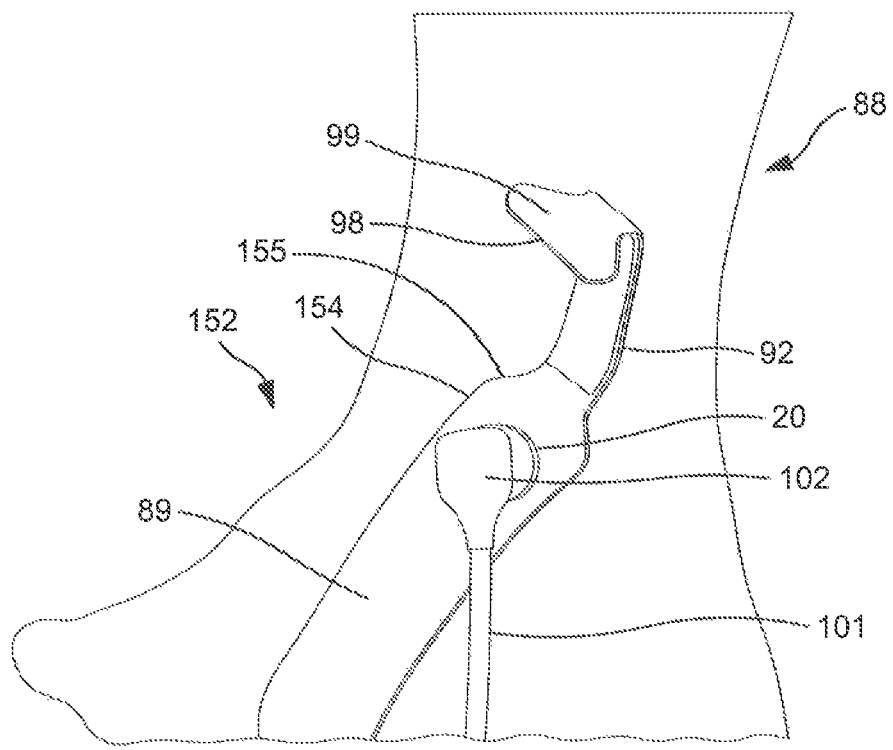
FIG. 10 shows the attachment of a cathode connector to the band and the folding of a tab on the band of FIG. 9 in accordance with one embodiment of the present disclosure.
Figure 11:
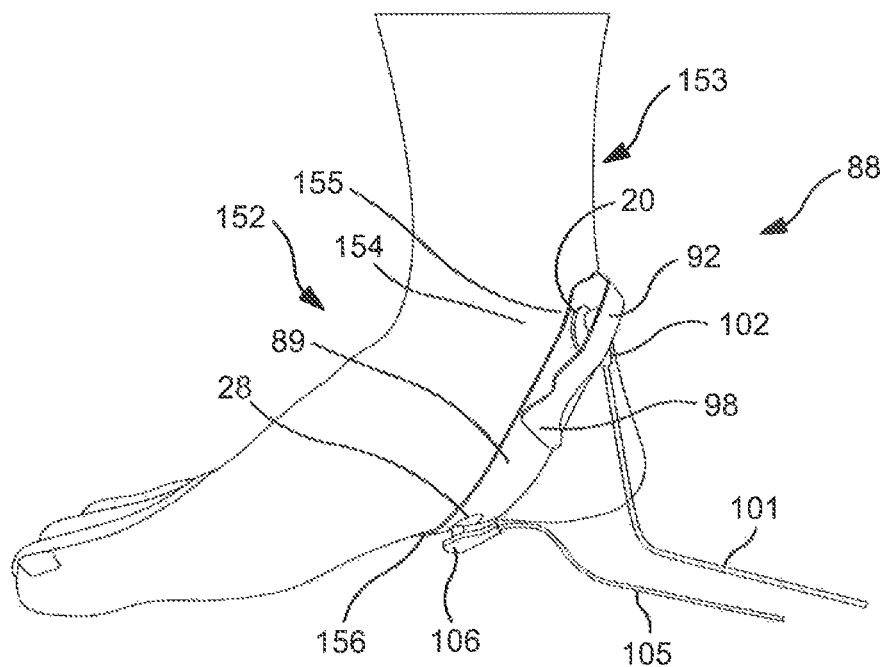
FIG. 11 shows the attachment of the tab of FIG. 10 to the band where a compression bead on the band is positioned over the cathode and cathode connector in accordance with one embodiment of the present disclosure.

Turning to FIG. 9, the attachment of the electrode band 88 to a non-glabrous skin surface, such as a surface proximate the medial malleolus 154 and at least partly overlying the flexor retinaculum 155, such as at its cephalic border, is shown. Such a location ensures sufficient contact with the cathode 20 for electrical nerve stimulation of a target nerve. The skin-contacting surface 96 of the electrode band 88 can be placed against the skin and an adhesive or other attachment means on the skin-contacting surface 96 ensures that the electrode band 88 stays securely in place. Prior to attachment, the first release liner 94 and the second release liner 95 of the disposable electrode band 88 (see FIGS. 7, 8(a), and 8(b)) can be removed to expose an adhesive or other attachments means on the skin-contacting surface 96. As shown in FIG. 9, the skin contacting surface 96 of the disposable electrode band 88 is exposed so that the stimulating electrode (e.g., cathode 20) can be adhered to the non-glabrous skin 160 over top the target nerve (e.g., posterior tibial nerve 150) at a location that can be about 5 centimeters proximate the medial malleolus 154, where the skin at least partly overlies the flexor retinaculum 155, such as at its cephalic border, and posterior to the tibia 151 (see FIG. 1). The skin contacting surface 96 of the disposable electrode band 88 can be applied to the skin surface between the stimulating electrode (e.g., cathode 20) and the ground electrode (e.g., anode or positive electrode 28), which can be placed on the glabrous skin 162 at the arch of the foot 156. Further, as shown in FIG. 10, with the electrode band 88 placed in the desired location, a cathode lead 101 can be attached to the cathode 20 by fitting a cathode connector 102 over the cathode head 21 (see FIG. 9). Further, an anode lead 105 can be attached to the anode 28 by fitting an anode connector 106 over the anode head 29 (see FIGS. 7 and 11). As also shown in FIG. 10, the electrode band 88 is placed on the skin such that the gel compression bead 92 and the tab 98 are not attached to the skin. Referring to FIG. 11, the tab 98 can be folded towards the anode 28 such that the gel compression bead 92 rests over the cathode 20 and cathode connector 102, and the tab 98 can then be secured to the outer-facing surface 89 of the electrode band 88. Such an arrangement between the compression bead, cathode connector 102, and cathode 20 ensures that the target nerve is sufficiently immobilized due to application of a predetermined amount of pressure to the cathode 20 and the flexor retinaculum 155 located beneath the cathode 20. Meanwhile, the anode 28 can be positioned at the arch 156 of the foot 152 as shown, although it is to be understood that the anode 28 can be positioned on any suitable glabrous or non-glabrous skin surface.

The electrode band 88 or a roll of electrode bands 90 of FIGS. 7-11 can be packaged in conjunction with a cathode lead 101, cathode connector 102, anode lead 105, and anode connector 106 in a kit for use in a medical professional's office or by the subject outside the medical professional's office (e.g., at home). The cathode lead 101 and anode lead 105 can then be connected to an electronic control system 60 (see FIG. 2) to provide electrical stimulation to a target nerve. Further, although not shown, it is to be understood that two electrode bands 88, two cathode connectors 102, two cathode leads 101, two anode connectors 106, and two anode leads 105 can be used in order to carry out bilateral electrical nerve stimulation, where a first electrode band is placed at one ankle proximate a first medial malleolus and can at least partly overlie a first flexor retinaculum, such as at its cephalic border, and a second electrode band is placed at the opposite ankle proximate the second medial malleolus and can at least partly overlie a second flexor retinaculum, such as at its cephalic border, of a subject.

Figure 12:
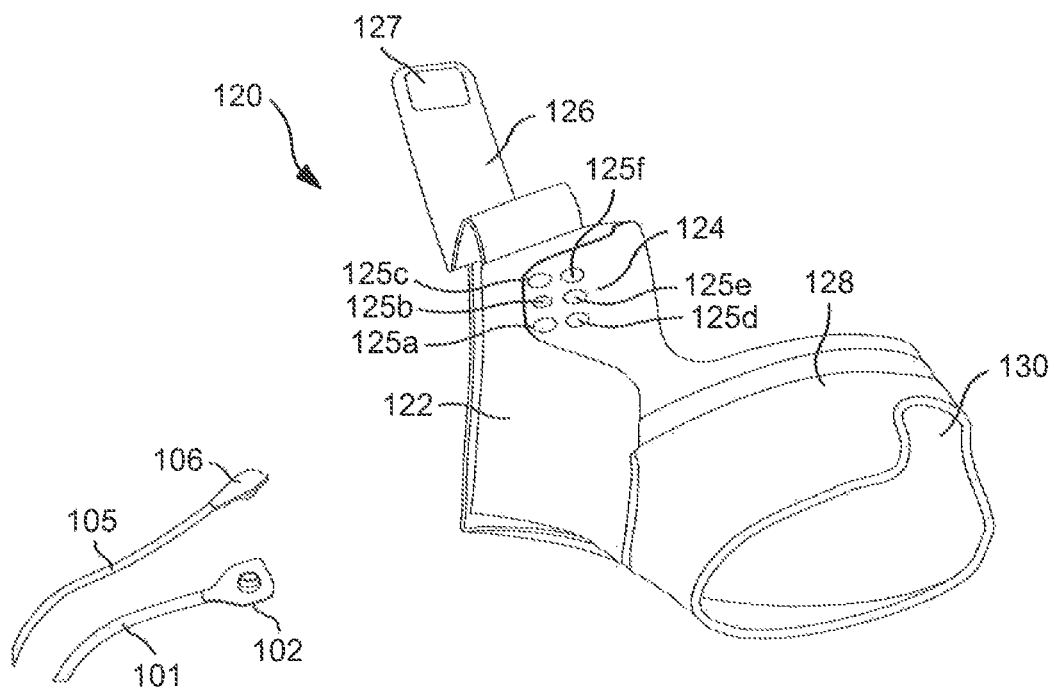
FIG. 12 shows another embodiment of a brace used for transcutaneously stimulating a target nerve in accordance with the present disclosure, along with anode and cathode leads.
Figure 13:
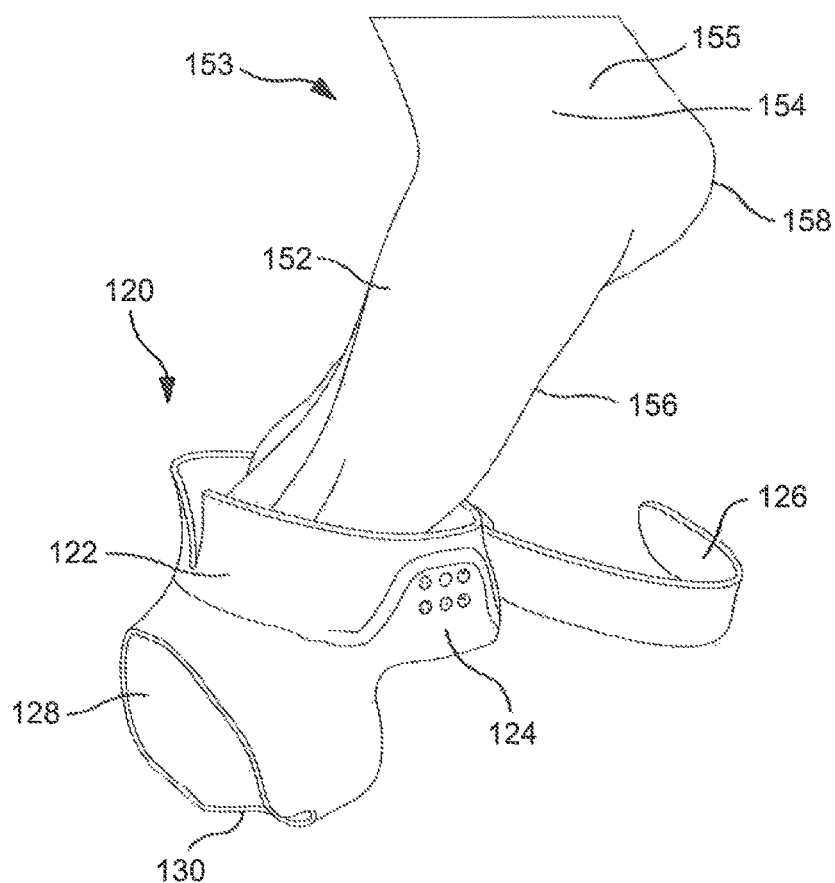
FIG. 13 shows the placement of the brace of FIG. 12 on a foot and ankle of a subject in accordance with one embodiment of the present disclosure.

In still another embodiment, referring to FIGS. 12-19, a separate cathode 20 and separate anode 28 (e.g., not part of an electrode band) can be used in conjunction with a brace 120 having particular features that ensure that the cathode 20 and anode 28 are placed in the appropriate location on a subject's skin for effective and consistent electrical nerve stimulation of a target nerve. The brace 120 can be made from a soft material that can be comfortable, breathable, and non-irritating when in contact with a subject's skin and foot, such as cotton, wool, polyester, rayon, GORE-TEX, etc. As shown in FIGS. 12 and 13, the brace 120 can include an ankle portion 122, a pre-perforated dot matrix 124 disposed on the ankle portion 122 having pre-perforated dots 125a, 125b, 125c, 125d, 125e, and 125f, a compressive strap 126, and a compressive strap attachment means 127. The compressive strap attachment means 127 can be a hook and loop type fastener such as a VELCRO™ fastener, a button, a snap, a hook, a pin, an adhesive, etc. The brace 120 can also include a foot portion 128 having a cut-out section 130. The ankle portion 122 can encircle the ankle 153 of a subject and can be configured to allow for formation of an opening in the ankle portion 122 proximate the subject's medial malleolus 154 to expose non-glabrous skin that overlies at least a part of the flexor retinaculum 155, such as at its cephalic border. Meanwhile, the foot portion 128 can encircle the foot 152 of a patient such that the cut-out section 130 exposes an arch 156 of the foot 152.

Figure 14:
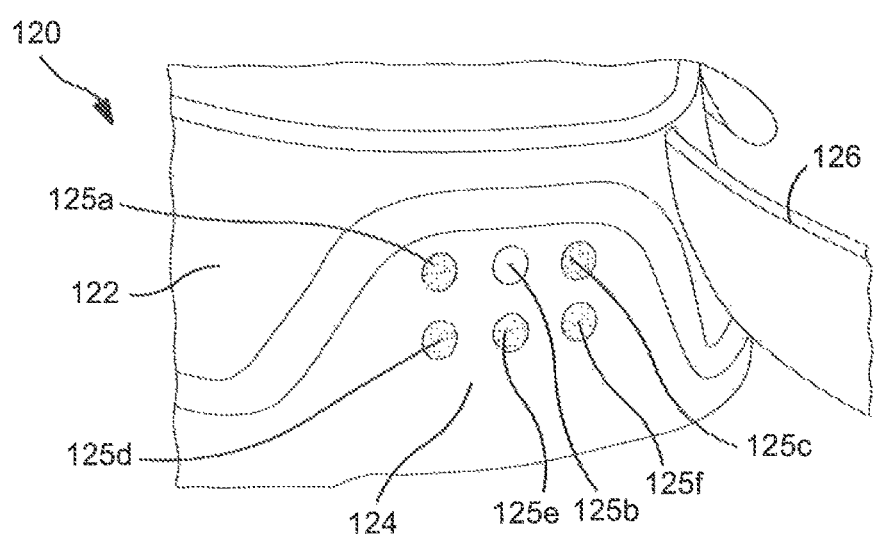
FIG. 14 is a partial view of the brace of FIG. 12 showing an opening through which a cathode can be exposed in accordance with one embodiment of the present disclosure.
Figure 15:
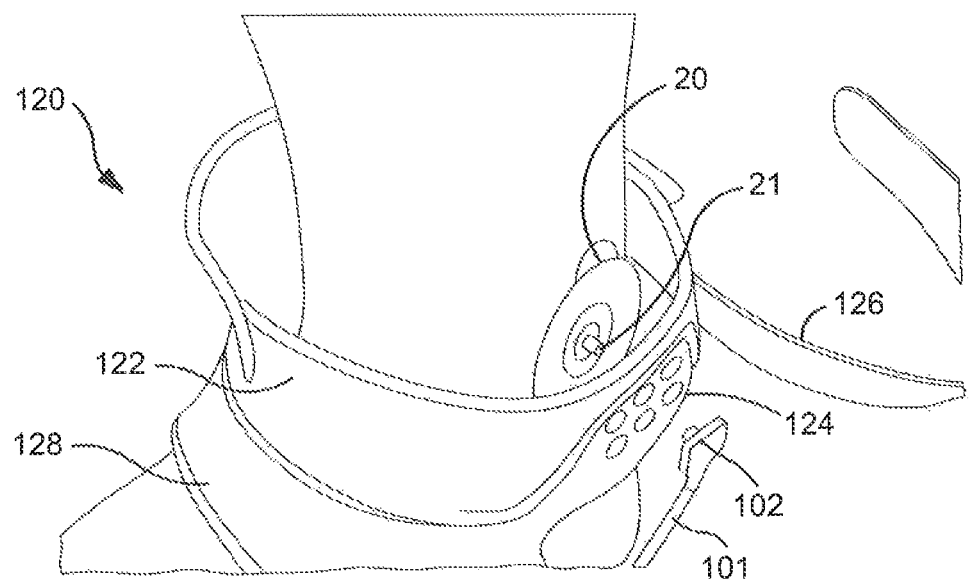
FIG. 15 is a partial view of the brace of FIG. 12 showing how the brace fits with a cathode, cathode connector, and cathode lead in accordance with one embodiment of the present disclosure.
Figure 16:
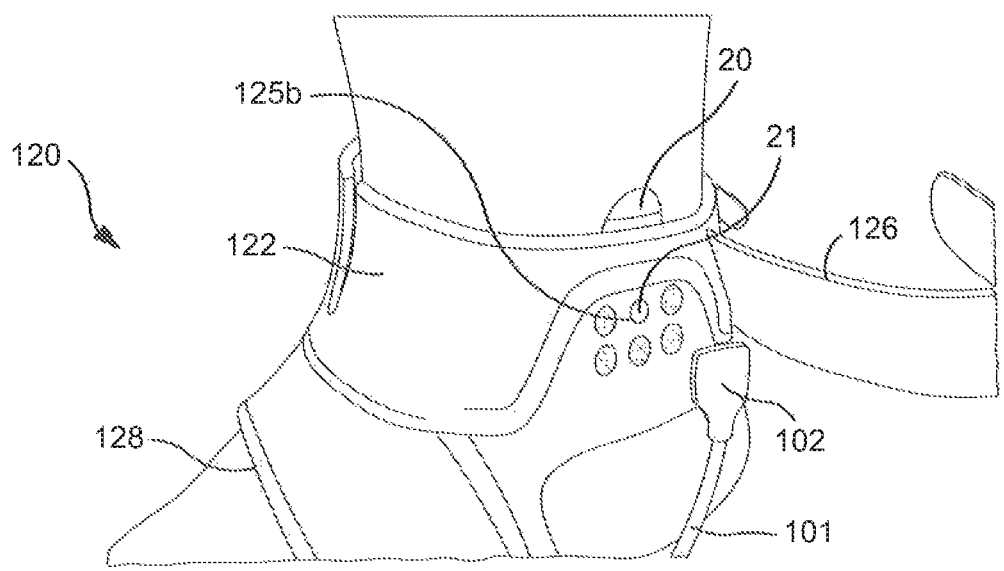
FIG. 16 is another partial view of the brace of FIG. 12 showing how an opening can be formed in the brace to enable the cathode to connect with the cathode connector.

Turning now to the pre-perforated dot matrix 124 specifically and referring to FIG. 14, the brace material inside one of the pre-perforated dots 125b located at ankle portion 122 of the brace 120 can be removed by a medical professional. Although the opening in FIG. 14 has been created by the removal of the material inside pre-perforated dot 125b, it is to be understood that, alternatively, a medical professional could remove material from dot 125a, dot 125c, dot 125d, dot 125e, or dot 125f depending on a particular subject's anatomy and the size and shape of the subject's medial malleolus 154, where the dot 125(a-f) from which material is removed is the dot 125(a-f) that is positioned closest to the subject's medial malleolus 154 and thus the location at which a cathode 20 can be placed. As such, the opening formed by removal of one of the dots 125(a-f) permits exposure of a cathode 20 so that a cathode lead 101 can be connected to the cathode 20 via at the cathode head 21 via a cathode connector 102 (see FIGS. 15 and 16).

Figure 18:
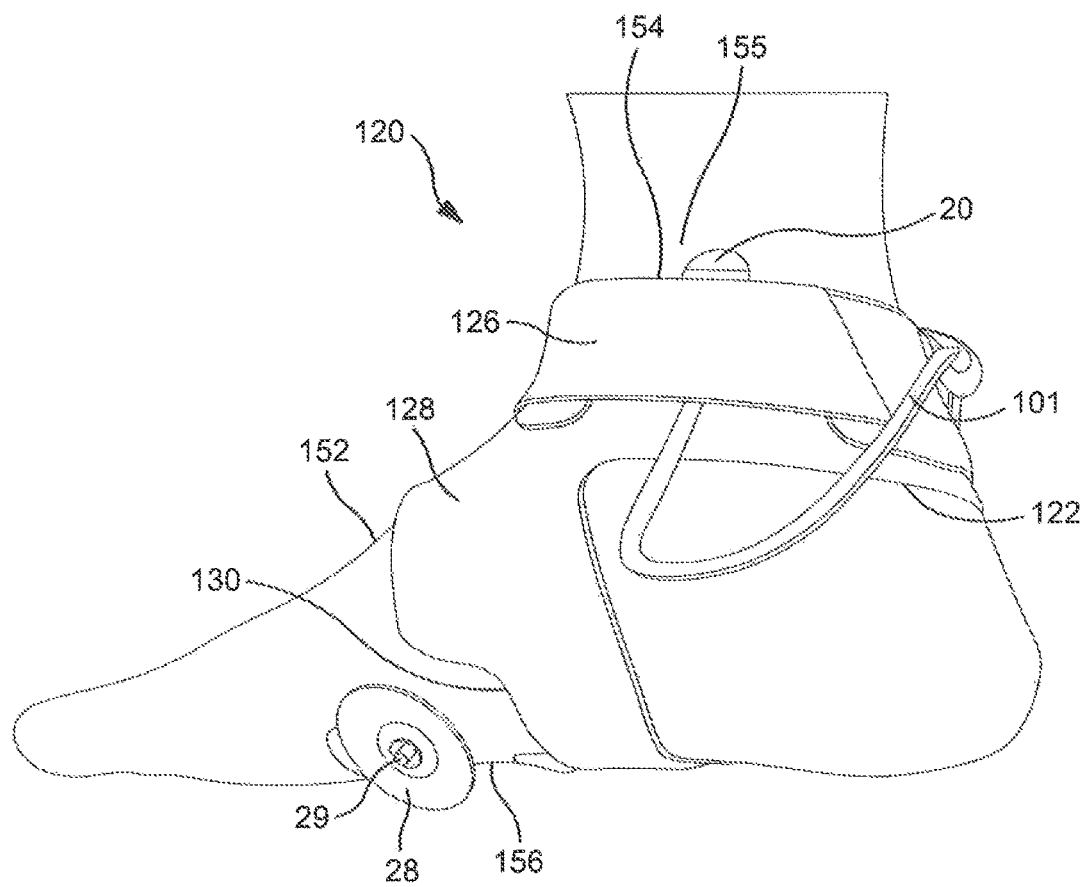
FIG. 18 shows how the brace of FIG. 12 is positioned on the foot in conjunction with an anode and a cathode.

Meanwhile, referring to FIG. 18, the cut-out section 130 in the foot portion 128 of the brace 120 allows for proper placement of an anode 28 having an anode head 29 on a subject's arch 156, where the arch 156 is a glabrous skin surface with low impedance which is ideal for the placement of the anode 28. The cut-out section 130 ensures that the anode head 29 is exposed for connection with an anode connector 106 that connects to anode lead 105.

Figure 17:
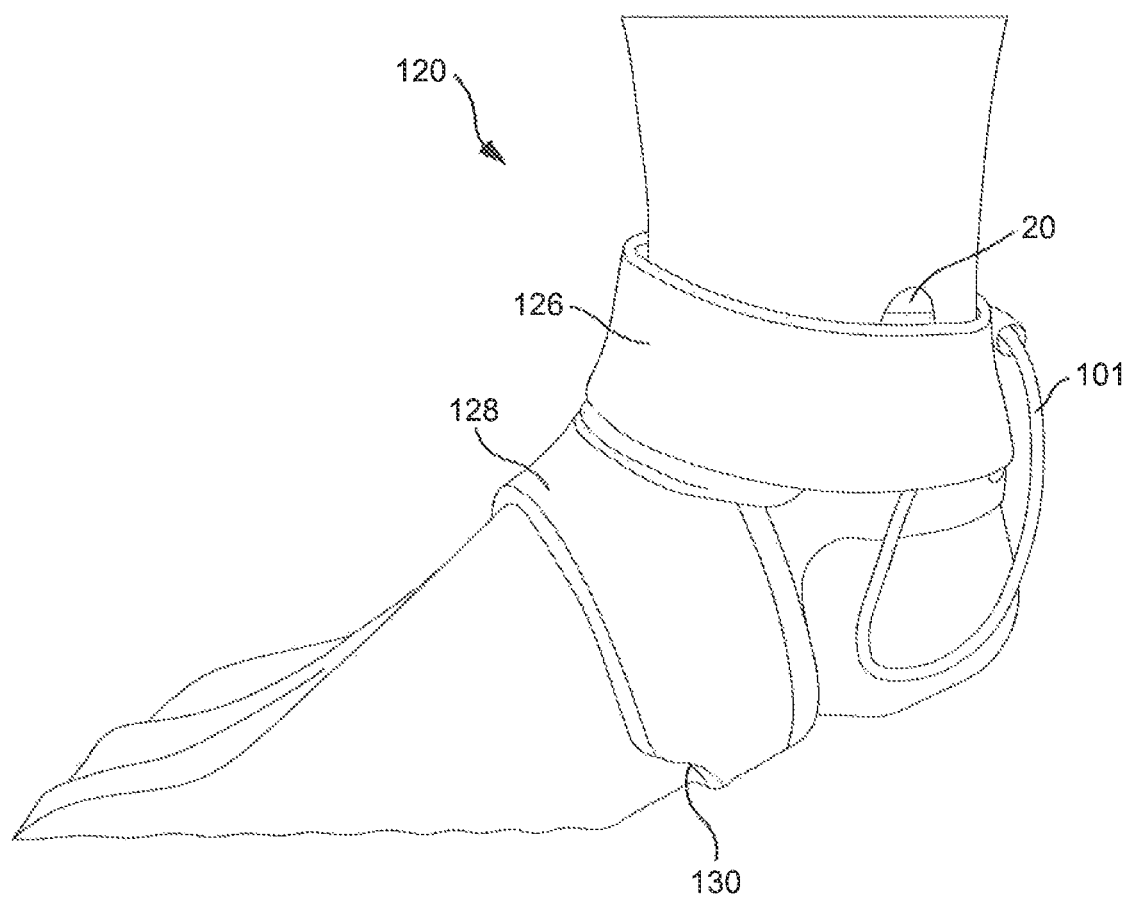
FIG. 17 shows how a compressive strap on the brace of FIG. 12 is positioned around an ankle portion of the brace.

Referring to FIGS. 11, 15 through 18, once the cathode 20 and anode 28 are positioned at the desired location of non-glabrous skin (e.g., at a surface of skin proximate the medial malleolus 154 and at least partly overlying the flexor retinaculum 155 for the cathode 20 and at the arch 156 for the anode 28), and the appropriate opening formed in the pre-perforated dot matrix 124 based on the position of the cathode head 21 on the subject's foot 152, the foot 152 can be inserted into the brace 120. Then, the cathode connector 102 attached to cathode lead 101 can be attached to the exposed cathode head 21 through the opening in the pre-perforated dot matrix 124 on the ankle portion 122 of the brace 120, and the anode connector 106 attached to anode lead 105 can be attached to the exposed anode head 29 near the cut-out section 130 of the foot portion 128 of the brace 120. Then, the compressive strap 126 can be wrapped around the ankle portion 122 and secured with attachment means 127. The compressive strap 126 is configured to apply a predetermined amount of pressure to the cathode 20 through cathode connector 102 to ensure that the target nerve being stimulated is sufficiently immobilized, which, in turn, allows for consistent and effective stimulation. FIGS. 17 and 18 show the brace 120 with the compressive strap 126 secured around the ankle. Although not shown in FIG. 18, the anode lead 105 can be connected to anode head 29 via an anode connector 106 (see FIG. 12), and then the monitoring and/or treatment methods discussed above can be carried out on the subject.

The brace 120 of FIGS. 12-18 can be packaged in conjunction with a cathode lead 101, cathode connector 102, anode lead 105, and anode connector 106 in a kit for use in a medical professional's office or outside the medical professional's office (e.g., at home). The cathode lead 101 and anode lead 105 can then be connected to an electronic control system 60 (see FIG. 2) to provide electrical stimulation to a target nerve. Such an embodiment as shown in FIGS. 12-18 allows for at home use by a subject without the direct supervision of a medical professional by ensuring proper placement of the cathode 20 and anode 28, which, in turn, ensures effective and consistent electrical nerve stimulation of the target nerve.

Figure 19:
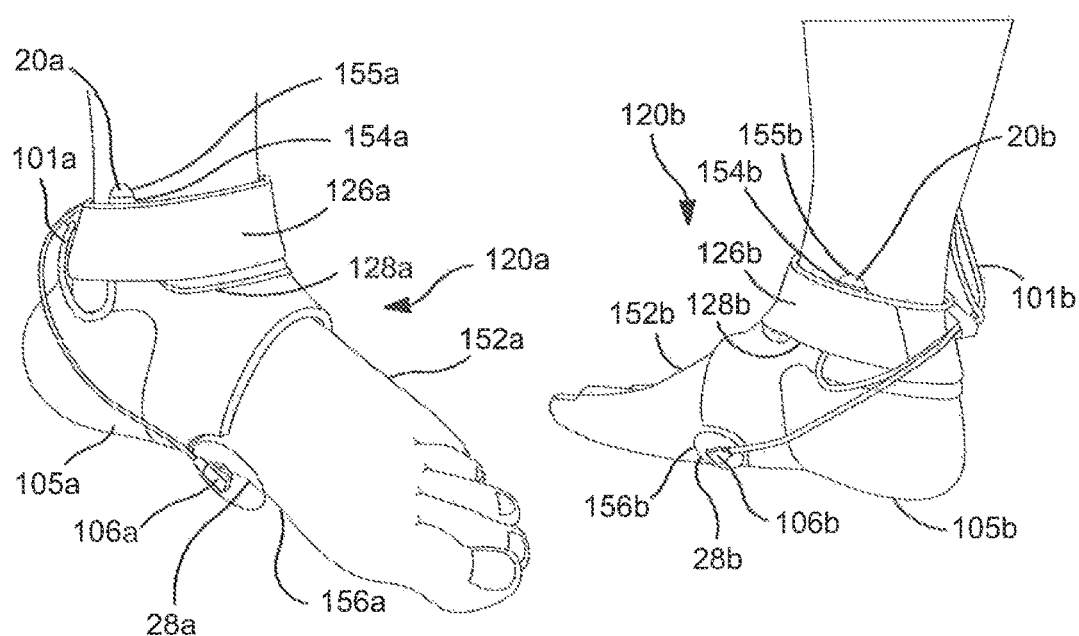
FIG. 19 shows one embodiment where two braces are utilized for transcutaneously stimulating a first target nerve and a second target nerve.

Further, as shown in FIG. 19, it is to be understood that two braces 120a and 120b having two ankle portions with two pre-perforated dot matrices (not shown), two compressive straps 126a and 126b, and two foot portions 128a and 128b, along with two cathode connectors 102a and 102b, two cathode leads 101a and 101b, two anode connectors 106a and 106b, and two anode leads 105a and 105b can be used in order to carry out bilateral electrical nerve stimulation, where a first brace 120a is placed on one foot of a subject and a second brace 120b is placed on the second foot of the subject, where cathodes 20a and 20b and anodes 28a and 28b are disposed at the appropriate location on foot 152a and foot 152*b*, respectively. For instance, cathodes 20*a* and 20*b* are placed at medial malleoli 154*a* and 154*b*, respectively, while anodes 28*a* and 28*b* are placed on arch 156*a* and 156*b*, respectively. As discussed above, bilateral electrical nerve stimulation can reduce the time of a treatment session, which results in more efficient treatment.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

What is claimed is:

1. A method for non-invasively monitoring a medical condition in a subject, the method comprising:
    positioning a first electrode adjacent to a surface of non-glabrous skin, wherein the non-glabrous skin is located at a first ankle of the subject proximate a first medial malleolus, wherein the first electrode is a cathode;
    positioning a second electrode adjacent to a surface of glabrous skin, wherein in the second electrode is an anode spaced apart a predetermined distance from the first electrode;
    transcutaneously delivering a first electrical nerve stimulation to a target nerve via the first electrode and the second electrode;
    determining a baseline current or a baseline voltage for the subject, wherein the baseline current is the current at which a sensory response or a motor response is elicited in the subject as a result of the first electrical nerve stimulation, and wherein the baseline voltage is the voltage at which a sensory response or a motor response is elicited in the subject;
    transcutaneously delivering a second electrical nerve stimulation to the target nerve via the first electrode and the second electrode;
    determining a threshold current or a threshold voltage for the subject, wherein the threshold current is the current at which a sensory response or a motor response is elicited in the subject as a result of the second electrical nerve stimulation, and wherein the threshold voltage is the voltage at which a sensory response or a motor response is elicited in the subject; and
    comparing the threshold current to the baseline current or the threshold voltage to the baseline voltage, wherein the medical condition is improved if the threshold current is lower than the baseline current or the threshold voltage is lower than the baseline voltage.

2. The method of claim 1, wherein the non-glabrous skin at least partly overlies a flexor retinaculum.

3. The method of claim 2, wherein the non-glabrous skin at least partly overlies a cephalic border of the flexor retinaculum.

4. The method of claim 1, further comprising positioning a compressive device over the first electrode to immobilize the target nerve.

5. The method of claim 4, wherein the compressive device includes a gel compression bead or a strap.

6. A system for non-invasively monitoring a medical condition in a subject via stimulation of a target nerve, the system comprising:
    a first electrode, wherein the first electrode is configured for placement on a surface of non-glabrous skin, wherein the non-glabrous skin is located at an ankle of the subject proximate a medial malleolus, wherein the first electrode is a cathode;
    a second electrode, wherein the second electrode is configured for placement on a surface of glabrous skin, wherein the second electrode is an anode; and
    an electronic control system coupled to the first electrode and the second electrode, wherein the electronic control system is configured to:
        transcutaneously deliver a first electrical nerve stimulation to the target nerve via the first electrode and the second electrode to determine a baseline current or a baseline voltage for the subject, wherein the baseline current is the current at which a sensory response or a motor response is elicited in the subject as a result of the first electrical nerve stimulation, and wherein the baseline voltage is the voltage at which a sensory response or a motor response is elicited in the subject; and
        transcutaneously deliver a second electrical nerve stimulation to the target nerve via the first electrode and the second electrode to determine a threshold current or a threshold voltage for the subject, wherein the threshold current is the current at which a sensory response or a motor response is elicited in the subject as a result of the second electrical nerve stimulation, and wherein the threshold voltage is the voltage at which a sensory response or a motor response is elicited in the subject, wherein the medical condition is improved if the threshold current is lower than the baseline current or the threshold voltage is lower than the baseline voltage.

7. The system of claim 6, wherein the non-glabrous skin at least partly overlies a flexor retinaculum.

8. The system of claim 7, wherein the non-glabrous skin at least partly overlies a cephalic border of the flexor retinaculum.

9. The system of claim 6, further comprising a compressive device, wherein the compressive device is configured for placement over the first electrode to immobilize the target nerve.

10. The system of claim 9, wherein the compressive device includes a gel compression bead or a strap.

11. The system of claim 6, further comprising a brace.

12. A method for treating a medical condition in a subject by transcutaneously delivering electrical nerve stimulation to the subject to stimulate a target nerve, the method comprising:
    positioning a first electrode adjacent to a surface of non-glabrous skin, wherein the non-glabrous skin is located at a first ankle of the subject proximate a first medial malleolus, wherein the first electrode is a cathode;
    positioning a second electrode adjacent to a surface of glabrous skin, where in the second electrode is a ground electrode spaced apart a predetermined distance from the first electrode; and
    transcutaneously delivering a first electrical nerve stimulation to the target nerve via the first electrode and the second electrode.

13. The method of claim 12, wherein the non-glabrous skin at least partly overlies a first flexor retinaculum.

14. The method of claim 13, wherein the non-glabrous skin at least partly overlies a cephalic border of the first flexor retinaculum.

15. The method of claim 12, further comprising stimulating a second target nerve, the method comprising:

positioning a third electrode adjacent to a surface of non-glabrous skin, wherein the third electrode is a cathode;

positioning a fourth electrode adjacent to a surface of non-glabrous or glabrous skin, wherein the fourth electrode is a ground electrode spaced apart a predetermined distance from the third electrode, wherein the fourth electrode is an anode; and transcutaneously delivering a second electrical nerve stimulation to the second target nerve through the third electrode.

16. A system configured to treat a medical condition in a subject by transcutaneously delivering electrical nerve stimulation to the subject to stimulate a first target nerve, the system comprising:

a first electrode, wherein the first electrode is configured for placement on a non-glabrous skin surface, wherein the non-glabrous skin is located at a first ankle of the subject proximate a first medial malleolus, wherein the first electrode is a cathode;

a second electrode, wherein the second electrode is configured for placement on a surface of glabrous skin, wherein the second electrode is an anode; and an electronic control system coupled to the first electrode and the second electrode, wherein the electronic control system is configured to transcutaneously deliver a first electrical nerve stimulation to the first target nerve via the first electrode and the second electrode.

17. The system of claim 16, wherein the non-glabrous skin at least partly overlies a first flexor retinaculum.

18. The system of claim 17, wherein the non-glabrous skin at least partly overlies a cephalic border of the first flexor retinaculum.

19. The system of claim 16, wherein the first target nerve emanates from the sacral plexus.

20. The system of claim 13, further configured to transcutaneously deliver electrical nerve stimulation to the subject to stimulate a second target nerve, the system comprising:

a third electrode, wherein the third electrode is configured for placement on a non-glabrous skin surface, wherein the third electrode is a cathode; and a fourth electrode, wherein the fourth electrode is configured for placement on a non-glabrous or glabrous skin surface, wherein the fourth electrode is an anode, wherein the third electrode and the fourth electrode are coupled to the electronic control system;

wherein the electronic control system is configured to transcutaneously deliver a second electrical nerve stimulation to the second target nerve via the third electrode and fourth electrode.

* * * * *